(12) United States Patent
Venkatraman et al.

(10) Patent No.: US 10,181,021 B2
(45) Date of Patent: Jan. 15, 2019

(54) METHOD AND APPARATUS FOR OFF-BODY DETECTION FOR WEARABLE DEVICE

(71) Applicant: Fitbit, Inc., San Francisco, CA (US)

(72) Inventors: Subramaniam Venkatraman, Walnut Creek, CA (US); Kevin Pu Weekly, San Leandro, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 29 days.

(21) Appl. No.: 15/012,607

(22) Filed: Feb. 1, 2016

(65) Prior Publication Data

US 2016/0154952 A1 Jun. 2, 2016

(51) Int. Cl.
| | |
|---|---|
| G06F 21/32 | (2013.01) |
| G06F 21/35 | (2013.01) |
| H04L 29/06 | (2006.01) |
| G06Q 20/32 | (2012.01) |
| G06Q 20/34 | (2012.01) |
| G06Q 20/40 | (2012.01) |
| G16H 40/63 | (2018.01) |
| H04W 4/80 | (2018.01) |
| G06F 19/00 | (2018.01) |

(52) U.S. Cl.
CPC .............. *G06F 21/32* (2013.01); *G06F 19/00* (2013.01); *G06F 21/35* (2013.01); *G06Q 20/3278* (2013.01); *G06Q 20/354* (2013.01); *G06Q 20/40145* (2013.01); *G16H 40/63* (2018.01); *H04L 63/0861* (2013.01); *H04W 4/80* (2018.02); *H04L 63/0492* (2013.01)

(58) Field of Classification Search
USPC ......................................... 600/547; 713/186
See application file for complete search history.

(56) References Cited

U.S. PATENT DOCUMENTS

| | | | |
|---|---|---|---|
| 6,695,207 B1 * | 2/2004 | Norris, Jr. ............... | B60R 25/23 235/380 |
| 8,684,900 B2 | 4/2014 | Tran | |

(Continued)

FOREIGN PATENT DOCUMENTS

| | | |
|---|---|---|
| WO | WO 12/170586 | 12/2012 |
| WO | WO 12/170924 | 12/2012 |

(Continued)

*Primary Examiner* — Tsan-Yu J Huang
(74) *Attorney, Agent, or Firm* — Knobbe, Martens, Olson & Bear, LLP

(57) ABSTRACT

A method and apparatus for capacitive off-wrist detection for wearable device are disclosed. In one aspect, the wearable device includes one or more biometric sensors including a capacitive sensor. The method may involve measuring, based on output of the capacitive sensor, a capacitance value indicative of proximity of the wearable device to a user. The method may also involve detecting a change in the capacitance value within a defined time interval, the change being greater than or equal to a threshold change indicative of the wearable device not being proximate to the user's skin. The method may further involve determining that the wearable device has been removed from the user in response to detecting that the change in the capacitance value within the defined time interval is greater than or equal to the threshold change.

28 Claims, 14 Drawing Sheets

(56) References Cited

U.S. PATENT DOCUMENTS

| | | | |
|---|---|---|---|
| 8,764,651 B2 | 7/2014 | Tran | |
| 2002/0184159 A1* | 12/2002 | Tadayon | G06Q 20/382 |
| | | | 705/54 |
| 2006/0284639 A1* | 12/2006 | Reynolds | G01D 5/24 |
| | | | 324/688 |
| 2008/0235144 A1* | 9/2008 | Phillips | G06Q 20/327 |
| | | | 705/67 |
| 2008/0287751 A1 | 11/2008 | Stivoric et al. | |
| 2009/0232362 A1* | 9/2009 | Otsubo | G06K 9/00026 |
| | | | 382/115 |
| 2013/0030320 A1* | 1/2013 | Maier | A61B 5/0531 |
| | | | 600/547 |
| 2014/0180022 A1 | 6/2014 | Stivoric et al. | |
| 2015/0026647 A1 | 1/2015 | Park et al. | |
| 2015/0070134 A1* | 3/2015 | Nagisetty | G07C 9/00111 |
| | | | 340/5.61 |
| 2015/0342527 A1* | 12/2015 | Karnik | A61B 5/6843 |
| | | | 600/408 |
| 2016/0154952 A1* | 6/2016 | Venkatraman | H04L 63/0861 |
| | | | 705/44 |
| 2016/0313176 A1* | 10/2016 | Lee | G01J 1/429 |

FOREIGN PATENT DOCUMENTS

| | | |
|---|---|---|
| WO | WO 12/171032 | 12/2012 |
| WO | WO 15/127067 | 8/2015 |
| WO | WO 16/003269 | 1/2016 |

\* cited by examiner

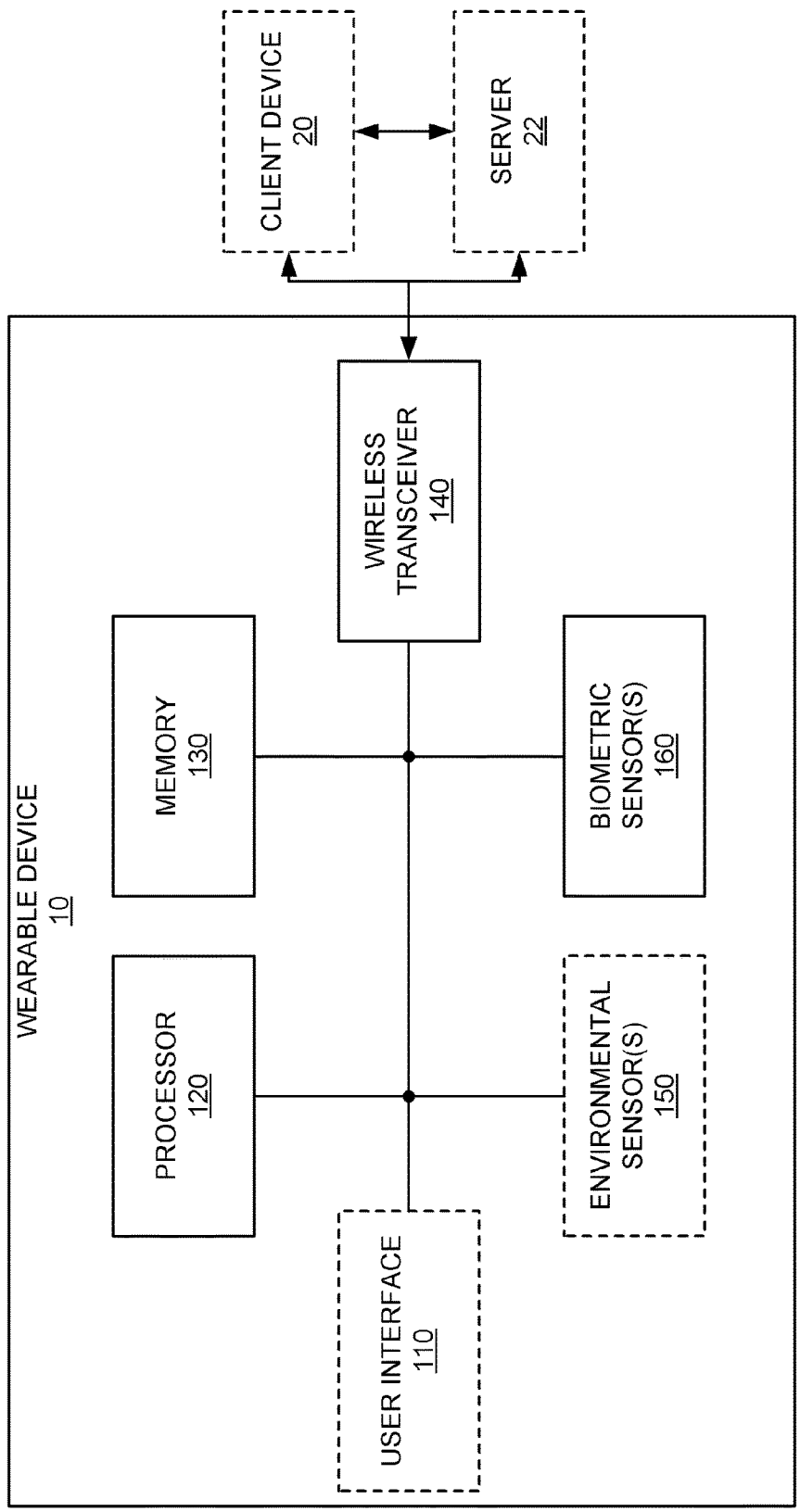

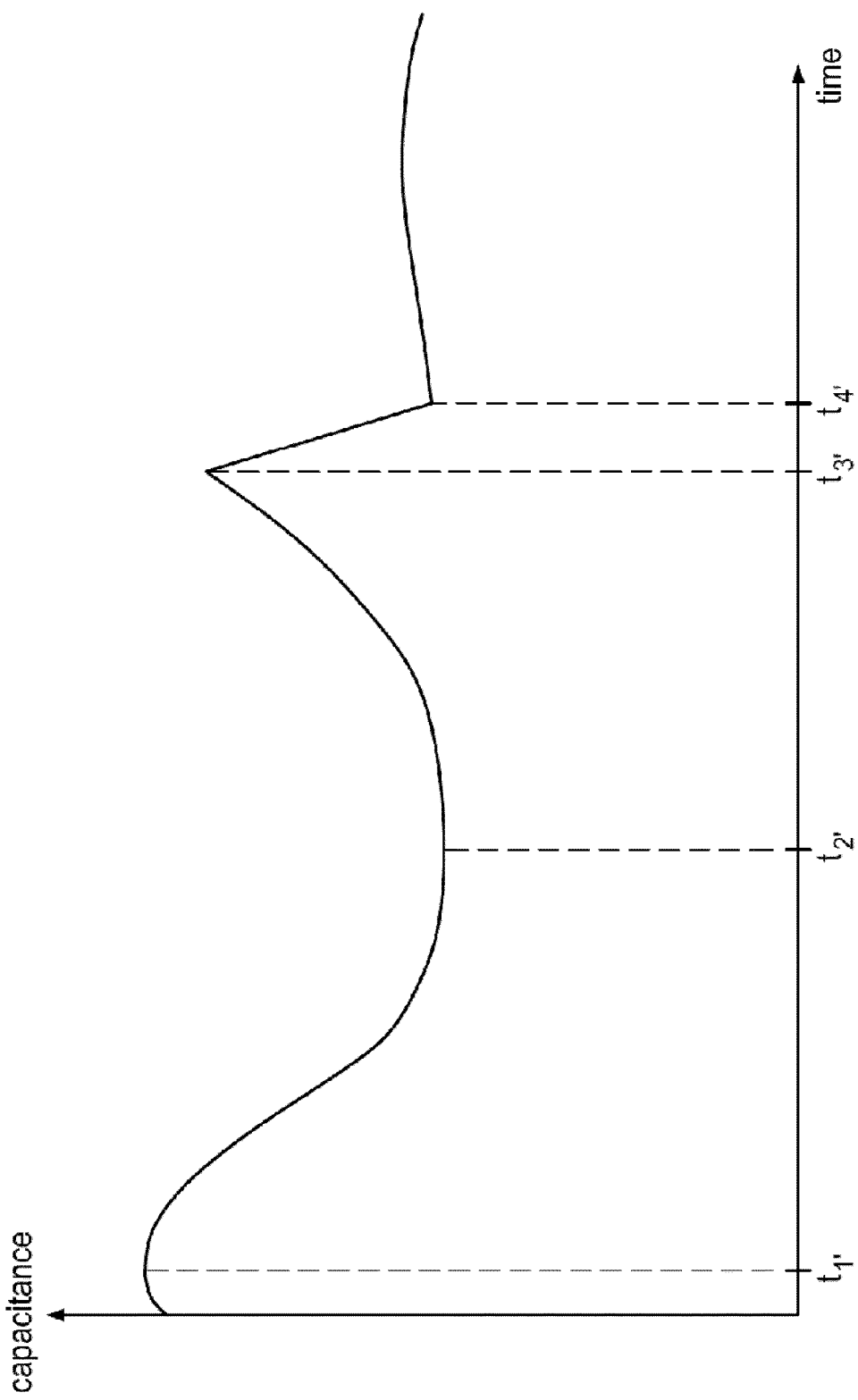

METHOD AND APPARATUS FOR OFF-BODY DETECTION FOR WEARABLE DEVICE

TECHNICAL FIELD

This disclosure related to the field of wearable devices, and particularly, to off-body detection for wearable devices.

BACKGROUND

Consumer interest in personal health has led to a variety of personal health monitoring devices being offered on the market. Such devices, until recently, tended to be complicated to use and were typically designed for use with one activity, for example, bicycle trip computers.

Advances in sensors, electronics, and power source miniaturization have allowed the size of personal health monitoring devices, also referred to herein as "biometric tracking," "biometric monitoring," or simply "wearable" devices, to be offered in extremely small sizes that were previously impractical. The number of applications for these devices is increasing as the processing power and component miniaturization for wearable devices improves.

In addition, wearable devices may be used to authenticate a user (e.g., via biometric input or a passcode), in order to authorize a user of the device to perform certain tasks. Such tasks may include mobile payments, keyless entry, etc. which may be performed when the user has been authenticated with the wearable device, but not when the user has been de-authenticated from the wearable device.

SUMMARY

The systems, methods and devices of this disclosure each have several innovative aspects, no single one of which is solely responsible for the desirable attributes disclosed herein.

In one aspect, there is provided a method of operating a wearable device, the wearable device comprising one or more biometric sensors including a capacitive sensor. The method may involve: measuring, based on output of the capacitive sensor, a capacitance value indicative of proximity of the wearable device to a user; and detecting a change in the capacitance value within a defined time interval, the change being greater than or equal to a threshold change indicative of the wearable device not being proximate to the user's skin. The method may further involve: determining that the wearable device has been removed from the user in response to detecting that the change in the capacitance value within the defined time interval is greater than or equal to the threshold change; and de-authenticating the user from the wearable device in response to determining that the wearable device has been removed from the user.

In another aspect, there is provided a method of operating a wearable device, the wearable device comprising one or more biometric sensors including an optical sensor and a capacitive sensor. The method may involve: detecting that an output signal of the optical sensor falls to or below an optical threshold indicative of the wearable device not being proximate to the user's skin; measuring, based on output of the capacitive sensor, a capacitance value indicative of proximity of the wearable device to the user; and detecting a change in the capacitance value within a defined time interval that is greater than or equal to a threshold change indicative of the wearable device not being proximate to the user's skin. The method may further involve: determining that the wearable device has been removed from the user in response to at least one of (i) detecting that the output signal of the optical sensor has fallen to or below the optical threshold and (ii) detecting that the change in the capacitance value within the defined time interval is greater than or equal to the threshold change; and de-authenticating the user from the wearable device in response to determining that the wearable device has been removed from the user.

In yet another aspect, there is provided a wearable device that includes a capacitive sensor configured to measure a capacitance value indicative of proximity of the wearable device to a user. The wearable device may further include at least one processor, and a memory storing computer-executable instructions for controlling the at least one processor to: detect that a change in the capacitance value within a defined time interval is greater than or equal to a threshold change indicative of the wearable device not being proximate to the user's skin; determine that the wearable device has been removed from the user in response to detecting that the change in the capacitance value within the defined time interval is greater than or equal to the threshold change; and de-authenticate the user from the wearable device in response to determining that the wearable device has been removed from the user.

In still another aspect, there is provided a wearable device that includes an optical sensor configured to monitor at least one biometric of a user, and a capacitive sensor configured to measure a capacitance value indicative of proximity of the wearable device to the user. The wearable device may further include at least one processor, and a memory storing computer-executable instructions for controlling the at least one processor to: detect that an output signal of the optical sensor falls to or below an optical threshold indicative of the wearable device not being proximate to the user's skin; detect that a change in the capacitance value within a defined time interval is greater than or equal to a threshold change indicative of the wearable device not being proximate to the user's skin; determine that the wearable device has been removed from the user in response to at least one of (i) detecting that the output signal of the optical sensor has fallen to or below the optical threshold and (ii) detecting that the change in the capacitance value within the defined time interval is greater than or equal to the threshold change; and de-authenticate the user from the wearable device in response to determining that the wearable device has been removed from the user.

BRIEF DESCRIPTION OF THE DRAWINGS

FIG. 1A is a block diagram illustrating certain components of an example wearable device in accordance with aspects of this disclosure.

FIGS. 7A and 7B are graphs illustrating examples of the capacitance measured by a capacitive sensor in accordance with aspects of this disclosure.

DETAILED DESCRIPTION

Figure 1B:
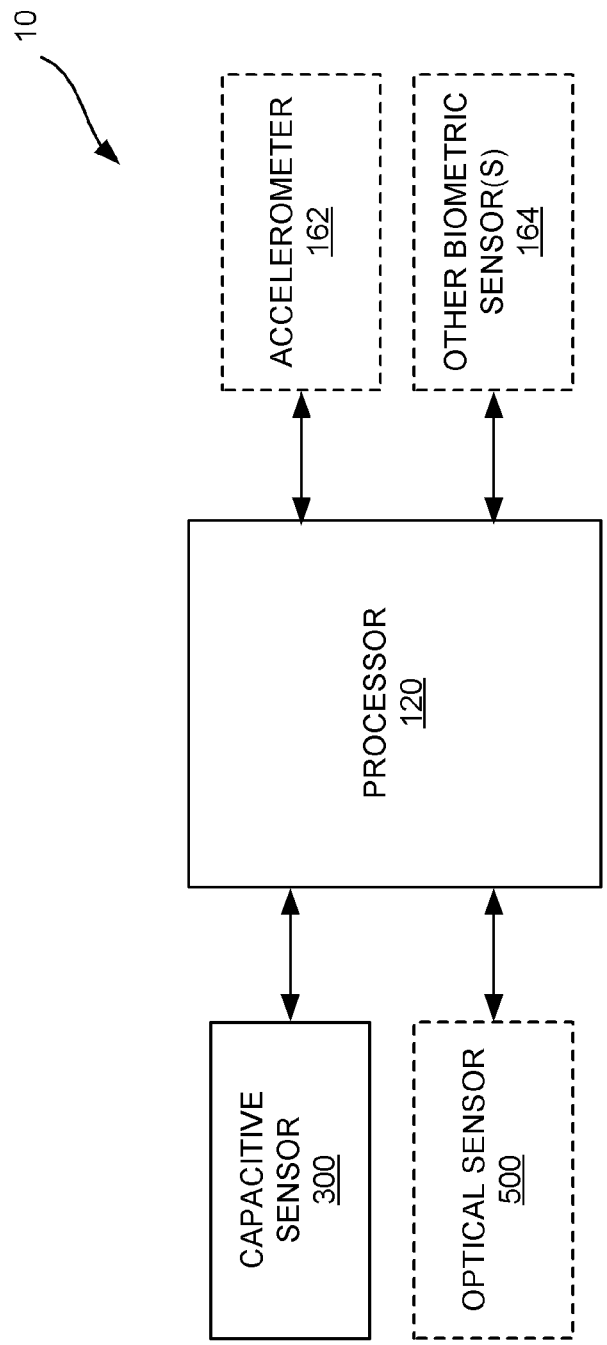
FIG. 1B is a block diagram illustrating example biometric sensors which may be in communication with a processor of a wearable device in accordance with aspects of this disclosure.

The detection of removal a wearable device from a user, which may be referred to as "off-wrist detection" in the case of a wearable device worn on the wrist, may be used by a processor of the wearable device as an input for certain processing routines. Although the term "off-wrist detection" may be used throughout this disclosure, the embodiments described herein may generally apply to the detection of removal of a wearable device from any location of a user's body. Thus, the present disclosure may equally apply to the removal of a wearable device from, for example, a user's ankle, arm, and/or leg. The term "off-wrist detection" is used interchangeably with the term "off-body detection" and should also be understood as being applicable to the detection of the removal of a wearable device from other locations on a user.

One example processing routine performed in response to off-wrist detection is the de-authorization of the wearable device from being used in the performance of certain tasks requiring authorization. As discussed above, wearable devices may be authorized by a user to be used as a payment device for mobile payments. For example, a wearable device may include a near field communication (NFC) chip which may store the user's credit card, debit card, and/or bank account information. When authorized, the user may scan the NFC chip by, for example, moving the wearable device within close proximity of an NFC reader, in order to make a payment. In this context, there remains a need to ensure de-authorization of a user from performing tasks such as mobile payments when the wearable device is no longer worn by the user in order to prevent such tasks from being performed by unauthorized parties.

Since a wearable device may be tied to a user's financial information, it is desirable to ensure that the wearable device cannot be used for mobile payments by an individual who is not associated with or authorized to use the stored financial information. This may be accomplished by de-authorizing the device, thereby preventing the device from being used for mobile payment. One method of de-authorizing a wearable device is to de-authorize the wearable device upon off-body detection, for example, when the user removes the device from his/her body (e.g., wrist). In other words, the user may be de-authenticated from using the wearable device to make mobile payments if the processor of the wearable device determines that the wearable device has been removed from the user.

Current approaches to off-wrist detection may not provide the level of security required for the handling of sensitive data, such as the type of information used for mobile payments. For example, certain off-wrist detection techniques may have a delay from the time the wearable device is removed from a user's wrist until the wearable device has confirmed the off-wrist event. During such a delay, it may be possible for a thief or unauthorized user to attach the wearable device to his/her wrist before the device has detected the off-wrist event, thereby leaving the wearable device authorized for mobile payments by the thief. One aspect of this disclosure provides techniques for ensuring that off-wrist events can be detected and/or confirmed quickly enough to prevent unauthorized mobile payments.

Although the above-description of off-wrist detection relates to mobile payments, the present disclosure is not so limited. Other applications for off-wrist detection may include determining the accuracy or confidence level of measured biometric signals such as heart rate, galvanic skin response, body temperature, etc. The accuracy or confidence level may then be used in excluding certain biometric signal measurements when analyzing the measured biometric signals, thereby increasing the accuracy and relevance of the analysis. Accordingly, if it is determined that the wearable device is off-wrist, then biometric signals measured after the off-wrist detection may be ignored or discarded, or the accuracy or confidence level of such signals may otherwise be flagged as questionable. There are many other applications for off-wrist detection which may be implemented in conjunction with this disclosure, such as, for example, keyless entry, electronic signatures (e-signatures), logging into a computer, etc., as described in further detail below.

Wearable Device Overview

FIG. 1A is a block diagram illustrating an example wearable device in accordance with aspects of this disclosure. The wearable device 10 may include a processor 120, a memory 130, a wireless transceiver 140, and one or more biometric sensor(s) 160. The wearable device 10 may also optionally include a user interface 110 and one or more environmental sensor(s) 150. The wireless transceiver 140 may be configured to wirelessly communicate with a client device 20 and/or server 22, for example, either directly or when in range of a wireless access point (not illustrated). Each of the memory 130, the wireless transceiver 140, the one or more biometric sensor(s) 160, the user interface 110, and/or the one or more environmental sensor(s) 150 may be in electrical communication with the processor 120. In some embodiments, the wireless transceiver 140 may include an NFC chip (which may be separately located from the remaining wireless circuitry of the wireless transceiver 140) for communication with an NFC reader. The NFC chip may be a powered or passive device. When the NFC chip is a powered device, the processor 120 may power off the NFC chip to disable the NFC chip's wireless communication functionality. In certain embodiments, the NFC chip may store information for performing mobile payments/transactions (e.g., credit card, debit card, and/or bank account information).

The memory 130 may store instructions for causing the processor 120 to perform certain actions. For example, the processor 120 may be configured to detect off-body events based on instructions stored in the memory 130. The processor may receive input from the one or more of the biometric sensor(s) 160 and/or the one or more environmental sensors 150 in order to determine whether the wearable device 10 has been removed from the user. In some embodiments, the biometric sensors 160 may include one or more of a capacitive sensor, an optical sensor (e.g., a photoplethysmographic (PPG) sensor), an accelerometer, and/or other biometric sensor(s). Further information regarding such biometric sensors are described in more detail below (e.g., in connection with FIG. 1B).

The wearable device 10 may collect one or more types of physiological and/or environmental data from the one or more biometric sensor(s) 160, the one or more environmental sensor(s) 150, and/or external devices and communicate or relay such information to other devices (e.g., the client device 20 and/or the server 22), thus permitting the collected data to be viewed, for example, using a web browser or network-based application. For example, while being worn by the user, the wearable device 10 may perform biometric monitoring via calculating and storing the user's step count using the one or more biometric sensor(s) 160. The wearable device 10 may transmit data representative of the user's step count to an account on a web service (e.g., www.fitbit.com), computer, mobile phone, and/or health station where the data may be stored, processed, and/or visualized by the user. The wearable device 10 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; location and/or heading (e.g., via a global positioning system (GPS), global navigation satellite system (GLONASS), or a similar system; elevation); ambulatory speed and/or distance traveled; swimming lap count; swimming stroke type and count detected; bicycle distance and/or speed; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 10 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and/or magnetic field. Furthermore, the wearable device 10 (and/or the client device 20 and/or the server 22) may collect data from the biometric sensor(s) 160 and/or the environmental sensor(s) 150, and may calculate metrics derived from such data. For example, the wearable device 10 (and/or the client device 20 and/or the server 22) may calculate the user's stress or relaxation levels based on a combination of heart rate variability, skin conduction, noise pollution, and/or sleep quality. In another example, the wearable device 10 (and/or the client device 20 and/or the server 22) may determine the efficacy of a medical intervention, for example, medication, based on a combination of data relating to medication intake, sleep, and/or activity. In yet another example, the wearable device 10 (and/or the client device 20 and/or the server 22) may determine the efficacy of an allergy medication based on a combination of data relating to pollen levels, medication intake, sleep and/or activity. These examples are provided for illustration only and are not intended to be limiting or exhaustive.

FIG. 1B is a block diagram illustrating a number of example biometric sensors that may be in communication with the processor of the wearable device in accordance with aspects of this disclosure. For example, in the embodiment of FIG. 1B, the wearable device 10 may include a capacitive sensor 300 which may be used for the detection of off-body events. The wearable device 10 may further include an optical sensor 500 (e.g., a PPG sensor), and may optionally include an accelerometer 162 and/or other biometric sensor(s) 164. Each of the biometric sensors illustrated in FIG. 1B is in electrical communication with the processor 120 to allow the processor 120 to determine whether the wearable device 10 has been removed from a user. The processor 120 may use input received from any combination of the capacitive sensor 300, the optical sensor 500, the accelerometer 162, and/or the other biometric sensor(s) 164 in detecting an off-body event. In some embodiments, the capacitive sensor 300, the optical sensor 500, the accelerometer 162, and/or the other biometric sensor(s) 164 may correspond to the biometric sensor(s) 160 illustrated in FIG. 1A.

Figure 2:
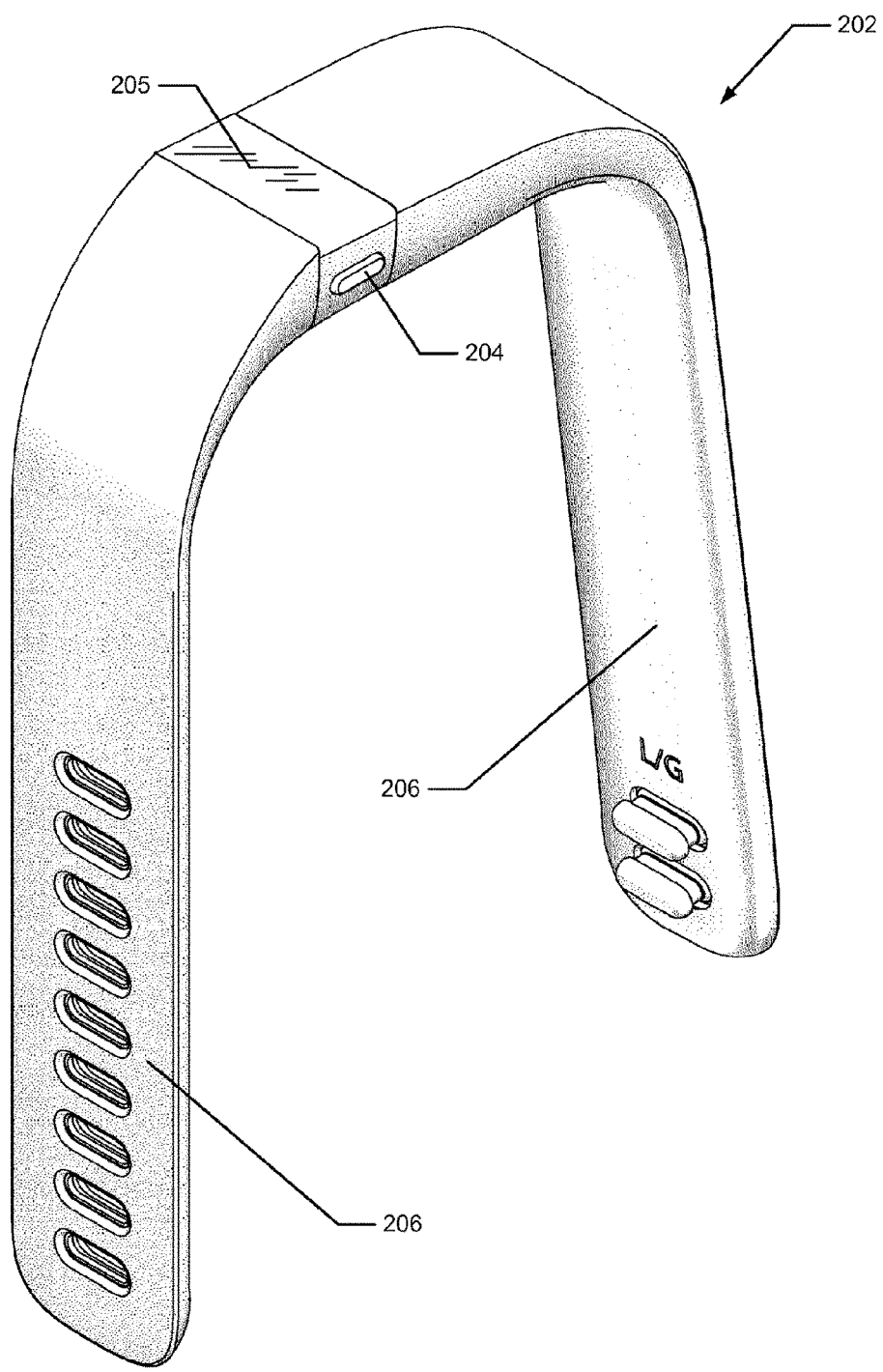
FIG. 2 is an example of a wrist-worn device in accordance with aspects of this disclosure.

The wearable device 10 according to embodiments and implementations described herein may have a shape and/or size adapted for coupling to (e.g., secured to, worn, borne by, etc.) the body or clothing of a user. FIG. 2 shows an example of a wrist-worn wearable device 202 in accordance with aspects of this disclosure. The wrist-worn wearable device 202 may have a display 205, button(s) 204, electronics package (not illustrated), and/or an attachment band 206. The attachment band 206 may be secured to the user through the use of hooks and loops (e.g., Velcro), a clasp, and/or a band having memory of its shape, for example, through the use of a spring metal band.

Figure 3:
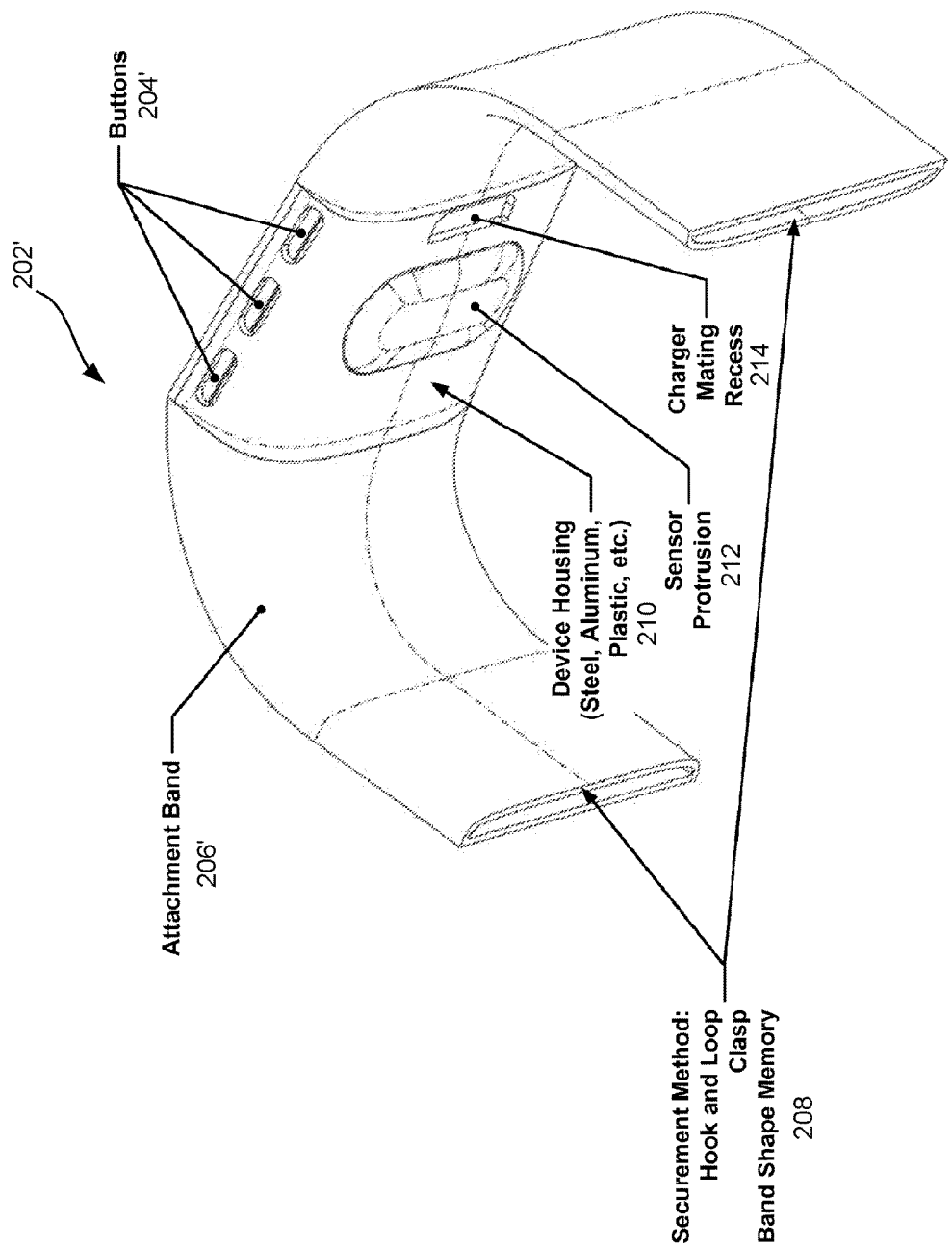
FIG. 3 is a perspective view illustrating another example of a wrist-worn device in accordance with aspects of this disclosure.

FIG. 3 is a perspective view illustrating another example of a wrist-worn device in accordance with aspects of this disclosure. The wrist-worn wearable device 202' of FIG. 3 may include button(s) 204', an attachment band 206', fasteners 208 (e.g., hook and loops, clasps, or band shape memory), a device housing 210, a sensor protrusion 212, and/or a charging/mating recess 214 (e.g., for mating with a charger or data transfer interface of a cable, etc.). In contrast to the wrist-worn wearable device 202 of FIG. 2, in FIG. 3, the wrist-worn wearable device 202' includes the sensor protrusion 212 and the recess 214 for mating with a charger and/or data transmission cable. FIG. 3 also illustrates the device housing 210 which may house internals of the wrist-worn wearable device 202' such as, for example, the processor 120, the capacitive sensor 300, the optical sensor 500, and/or the accelerometer 162. The optical sensor 500 may be housed directly below the sensor protrusion 212. Each of the capacitive sensor 300 and the optical sensor 500 are described in further detail below in connection with FIGS. 4 to 9B.

Certain implementations of off-body detection in accordance with this disclosure employ the use of a capacitive sensor 300 for the detection of off-wrist events. Capacitive sensors are utilized in applications such as capacitive touchscreens and radio frequency (RF) power modulation for tablets and smartphones. However, in the context of wearable devices 10 (e.g., smartwatches and activity trackers), capacitive sensors, which may be used to detect the human body, may be required to detect a much smaller capacitance change than in other applications of capacitive sensors. In addition to the size of the sensing electrode required to be integrated within a capacitive sensor 300 into the body of a wearable device 10, manufacturing and aesthetic considerations of the wearable device 10 may limit how close the internal sensing electrode of the capacitive sensor 300 may be positioned with respect to the human body when the wearable device 10 is worn. Wearable devices 10 may also experience a high amount of motion, particularly when the user is exercising. This may introduce variability into capacitive off-body detection as this motion may result in large transients in the capacitive sensor output (see, e.g., FIGS. 7A and 7B and the related description below). The magnitude of these transients may approach the normal signal deflection of a device being taken off the body, and thus the motion-induced noise in the capacitive sensor output may be incorrectly determined or interpreted to be an off-body event. This variability may be accounted for by certain aspects of the present disclosure, including algorithms (see, e.g., FIG. 10 and the related description) and information from optical sensor(s) (e.g., the optical sensor 500) in order to augment the off-body detection with additional information, and thereby improve the accuracy of the on/off-body detection of the wearable device 10.

Capacitive Sensor

Figure 4:
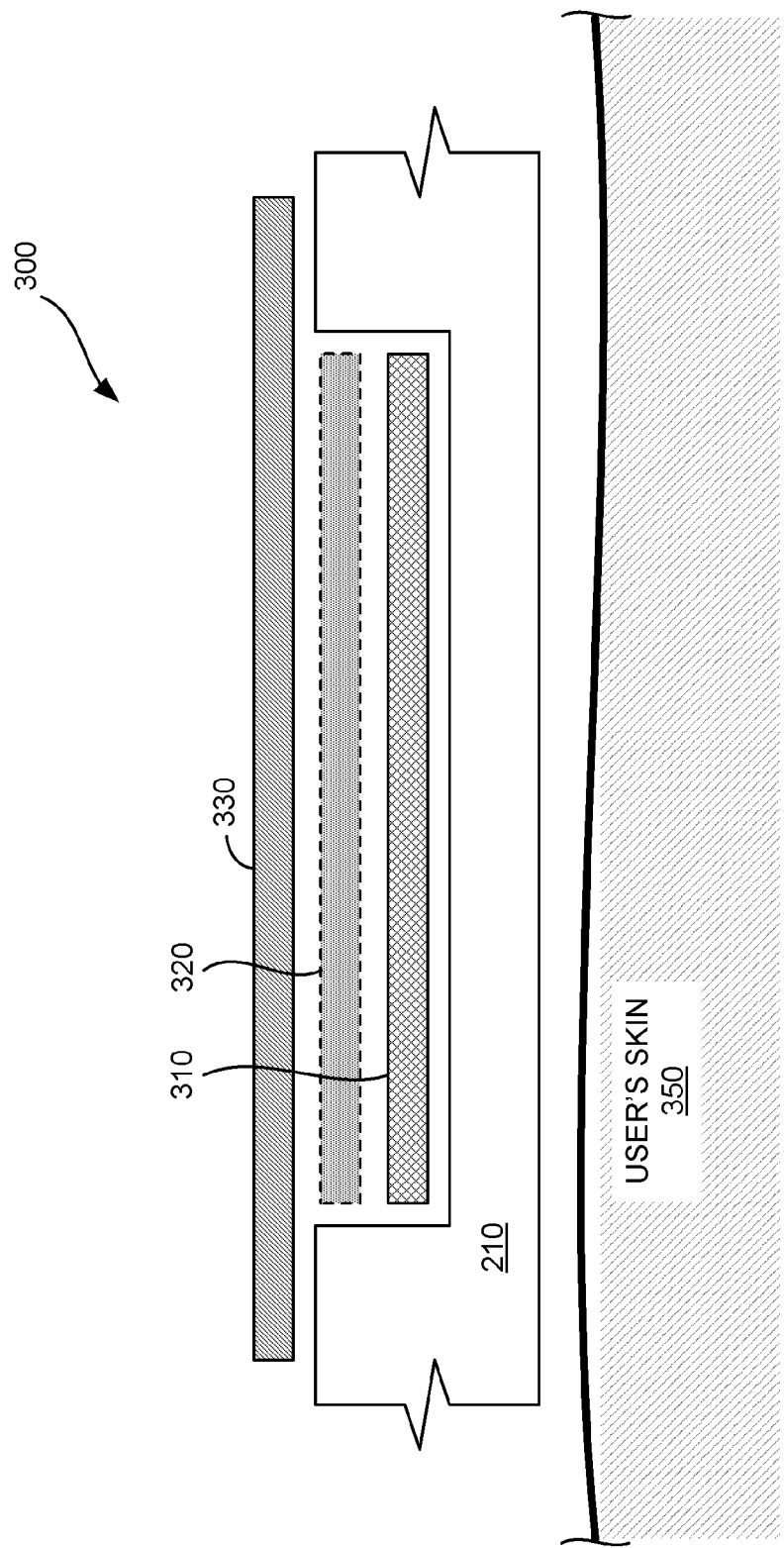
FIG. 4 is a cross-sectional view of a wearable device including a capacitive sensor in accordance with aspects of this disclosure.

FIG. 4 is a cross-sectional view of a portion of an example wearable device that includes a capacitive sensor in accordance with aspects of this disclosure. As shown in FIG. 4, the capacitive sensor 300 may be housed within a device housing 210. The device housing 210 may also be referred to herein as a device exterior or device body. The capacitive sensor 300 may include a capacitive sensor electrode 310, an optional active shield 320, and a ground plane 330. When the wearable device 10 is worn by a user, the device exterior 210 may be placed adjacent to the user's skin 350.

Figure 5:
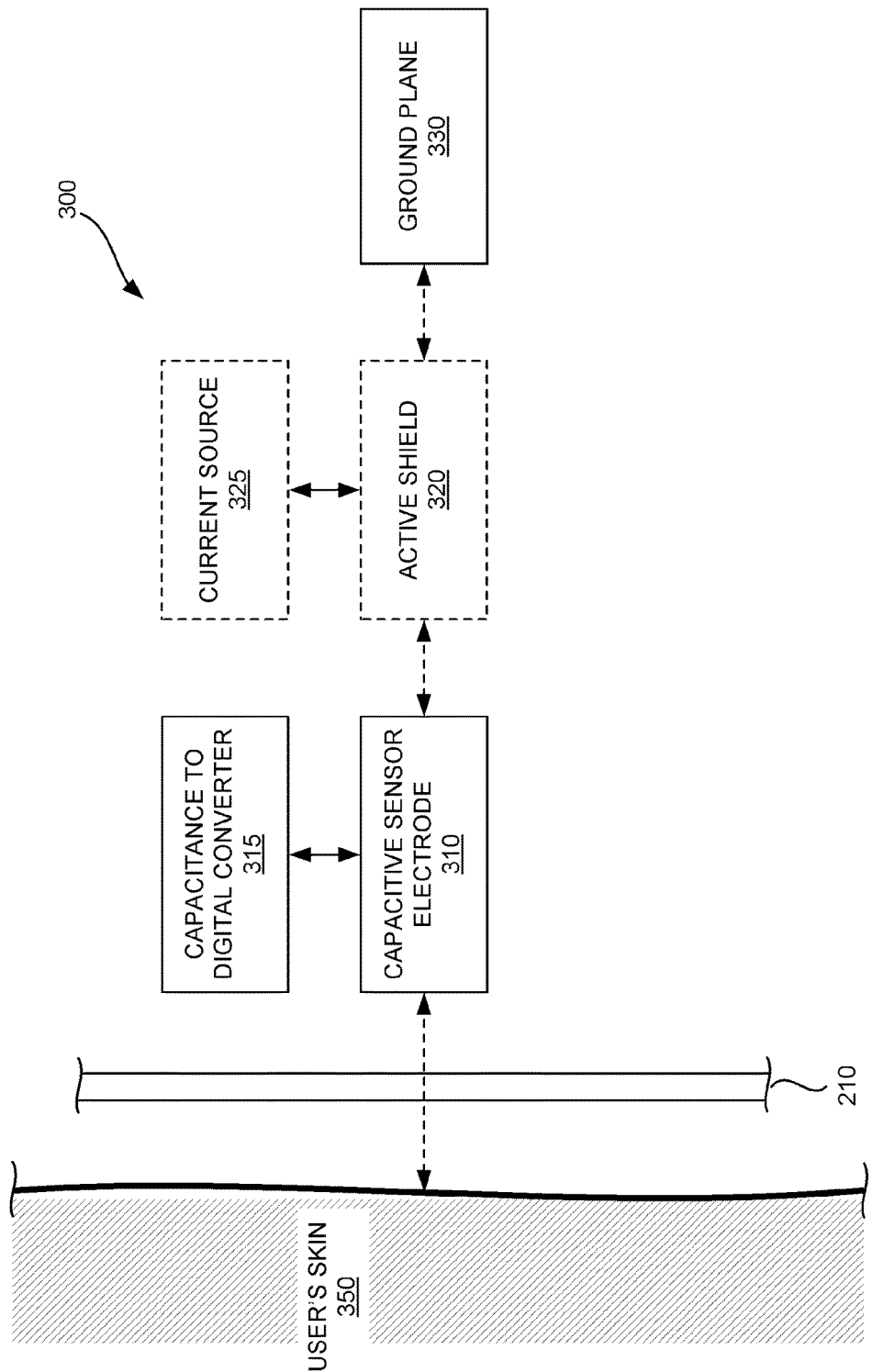
FIG. 5 is a block diagram illustrating example features of a wearable device, including a capacitive sensor, in accordance with aspects of this disclosure.

FIG. 5 is a block diagram illustrating certain components of another example wearable device that includes a capacitive sensor in accordance with aspects of this disclosure. With reference to FIG. 5, the capacitive sensor 300 may include a capacitive sensor electrode 310, a capacitance to digital converter (CDC) 315, an optional active shield 320, an optional current source 325, and a ground plane 330. Although the capacitive sensor 300 may be referred to for convenience as including each of the capacitive sensor electrode 310, the CDC 315, the active shield 320, the ground plane 330, etc., this disclosure is not so limited. For example, the active shield 320, current source 325, and ground plane 330 may be considered separate elements from the capacitive sensor 300 or may be omitted from the wearable device 10 entirely.

Figure 6:
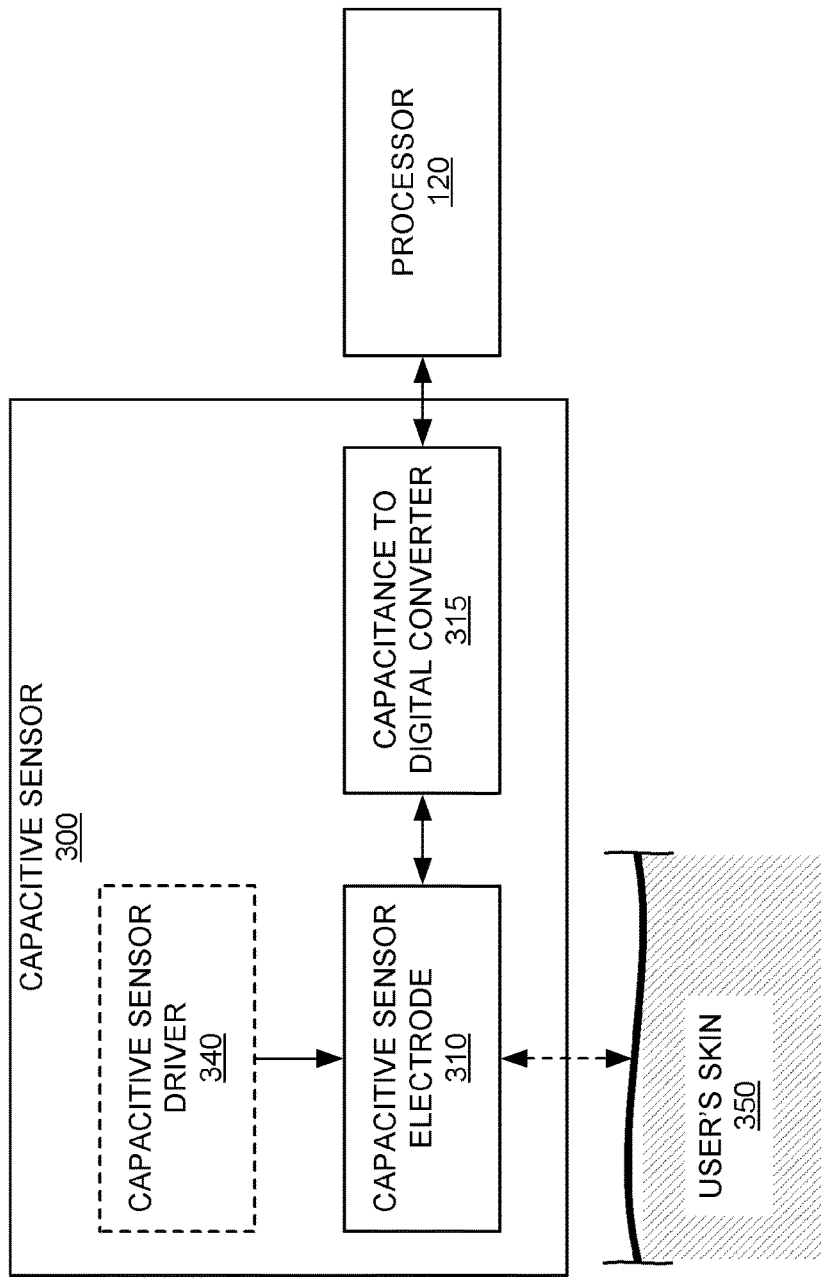
FIG. 6 is a block diagram illustrating another example of features of a wearable device, including a capacitive sensor, in accordance with aspects of this disclosure.

FIG. 6 is a block diagram illustrating certain components of yet another example wearable device that includes a capacitive sensor in accordance with aspects of this disclosure. With reference to FIG. 6, the capacitive sensor 300 may include a capacitive sensor electrode 310, a CDC 315, and an optional capacitive sensor driver 340. The CDC 315 may drive the capacitive sensor electrode 310 and receive an output signal from the capacitive sensor electrode 310. The CDC 315 may output a digital signal representative of capacitance measured by the capacitive sensor electrode 310 to the processor 120. Although FIGS. 4 to 6 illustrate a number of different components and configurations of the capacitive sensor, any combination of the illustrated components may be included in other implementations of the capacitive sensor 300.

Returning to FIG. 4, the device exterior 210 may be interposed between the user's skin 350 and the capacitive sensor 300. Accordingly, the capacitive sensor 300 may be protected from the external environment via the device exterior 210. The capacitive sensor plate or electrode 310 may be located adjacent to the device exterior 210 in order to be capacitively coupled with the user's skin 350. In one embodiment, the sensor electrode 310 is constructed via forming a copper area on a printed circuit board (PCB) internal to the wearable device 10 and the copper area may be placed to be close to the device exterior 210. The capacitive sensor electrode 310 may experience a change in capacitive value based on the proximity of the user's skin 350 to the capacitive sensor electrode 310. The active shield 320 may be located over the capacitive sensor electrode 310, and the ground plane 330 may be located over the active shield 320. The ground plane 330 shields the capacitive sensor electrode 310 from the other components of the wearable device 10, such as the processor 120 and/or other biometric sensor(s) 160. As such, the ground plane 330 may suppress the effects of electrical noise generated by electrical components of the wearable device 10 from interfering with the capacitance measurement performed by the capacitive sensor 300. The ground plane 330 may also protect the other components of the wearable device 10 from electrical noise radiated from the capacitive sensor electrode 310, for example, during a capacitive measurement.

The dashed arrows shown in FIGS. 5 and 6, illustrate capacitive coupling between the various components. For example, the user's skin may be capacitively coupled with the capacitive sensor electrode 310 when within a certain distance from the capacitive sensor electrode 310. Further, each of the active shield 320 and the ground plane 330 may be capacitively coupled to the capacitive sensor electrode 310. With reference to FIGS. 4 and 5, certain operations performed by the CDC 315 may be impaired by the ground plane 330 being located near the sensor electrode 310. As such, in at least one embodiment, the active shield 320 may be interposed between the capacitive sensor electrode 310 and the ground plane 330. The current source 325, which may be integrated into the CDC 315 in certain embodiments, may drive the active shield 320 to substantially the same potential as the capacitive sensor electrode 310. This may effectively remove capacitive coupling between the capacitive sensor electrode 310 and the ground plane 330, thereby allowing the capacitive sensor 300 to have higher measurement sensitivity.

Referring to FIG. 6, the capacitive sensor 300 may measure a capacitive value that is indicative of the proximity of a conductive object, such as the user's body 350, to the capacitive sensor electrode 310. In one implementation, the capacitive sensor 300 may include the capacitive sensor driver 340 that drives the capacitive sensor electrode 310 by applying a defined amount of charge to the capacitive sensor electrode 310. In certain implementations, the capacitive sensor driver 340 may be incorporated into the CDC 315. The CDC 315 may measure the capacitance of the capacitive sensor electrode 310 in response to the capacitive sensor driver 340 driving the capacitive sensor electrode 310. The processor 120 may receive the measured capacitance from the CDC 315.

The capacitance of the capacitive sensor electrode 310 may change in response to the conductive object being moved closer or further from the capacitive sensor electrode 310. Accordingly, the processor 120 may be configured to detect the proximity of the conductive object (e.g., the user's skin) in response to a change in capacitance measured by the capacitive sensor 300. The capacitance measured by the capacitive sensor 300 increases as the conductive object moves or is brought closer to the sensor electrode 310 and decreases when the conductive object moves or is taken away from the sensor electrode 310. There may be challenges in measuring or calibrating absolute values of capacitance measured by the capacitive sensor 300, which may represent on-wrist and off-wrist states, due to the dynamic nature of the dielectric material properties which may affect the capacitance measured by the capacitive sensor 300. For example, the dielectric material properties of the air or environment, the device exterior 210, and/or any glues used to manufacture the wearable device 10 may each have an effect on the capacitance measured by the capacitive sensor 300. Furthermore, there may be manufacturing and/or day-to-day variations (e.g., variations in temperature and humidity) which may significantly impact capacitance measurements.

Figure 7A:
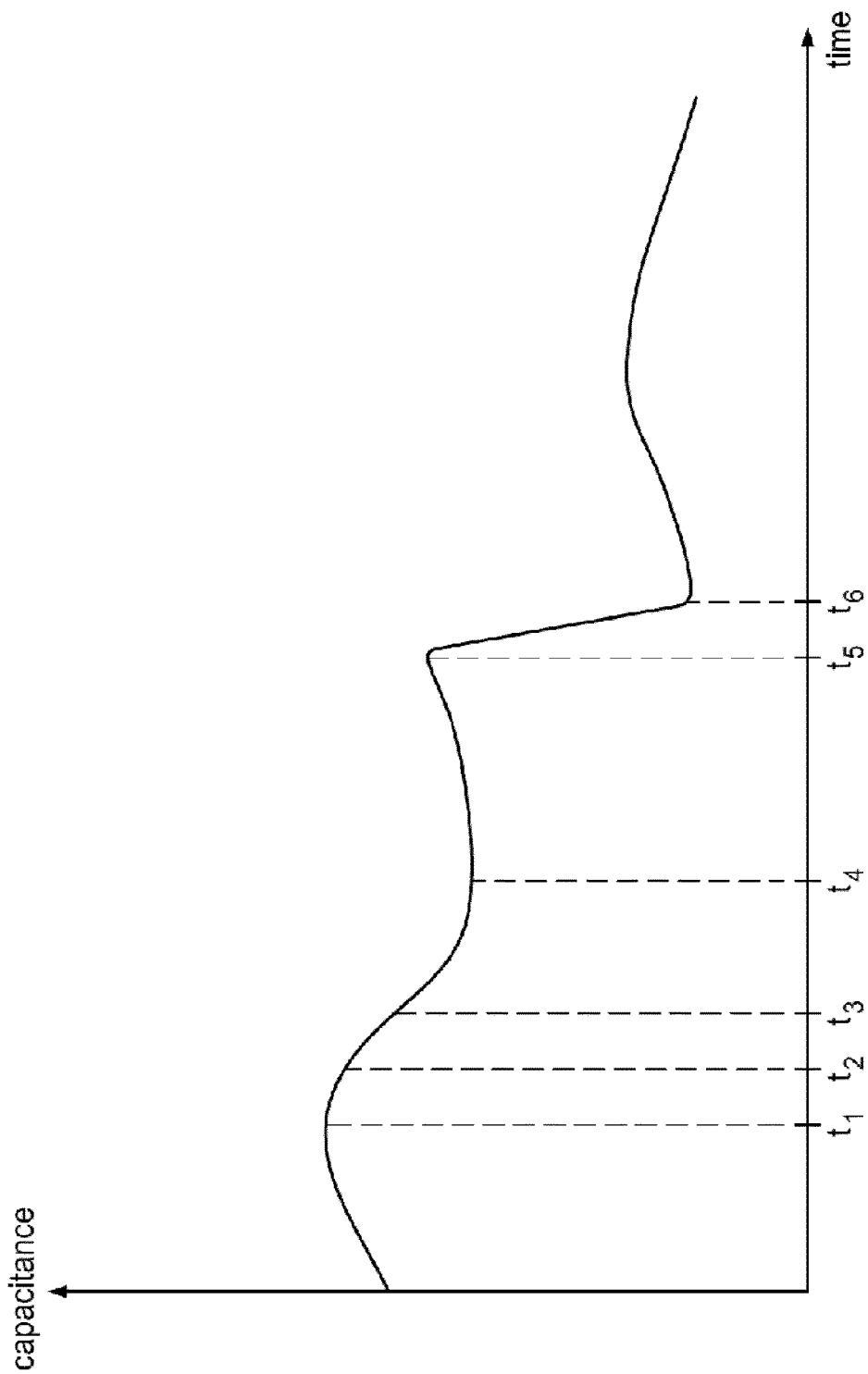

FIGS. 7A and 7B are graphs illustrating example capacitance values that may be measured by a capacitive sensor in accordance with aspects of this disclosure. The variations in the measured capacitance are illustrated by the fluctuations in the capacitance value. One method of distinguishing changes in the measured capacitance that are due to typical variations in the capacitance from those changes that are due to the wearable device 10 being removed from the user's body is to identify short-term changes in the measured capacitance, such as those that are generated when a conductive object (e.g., the skin on a user's wrist) is suddenly brought close or taken away from the device.

In one embodiment, these short-term changes in the capacitance may be identified by the processor 120 by applying a low-pass filter to the measured capacitance and then comparing any changes in the filtered signal to a threshold value. A low-pass filter may be used to remove (e.g., attenuate) high frequency signals generated due to noise or other high frequency fluctuations in the measured capacitance. Thus, the signal remaining after applying the low-pass filter to the measured capacitance may be a more accurate representation of the capacitance due to proximity of the wearable device 10 to the user's body. The threshold value may be an off-wrist threshold value that is indicative of the wearable device 10 not being proximate to the user's body. For example, the off-wrist threshold value may be a capacitance value that is set based on capacitive measurements taken when the wearable device 10 is not being worn by the user.

In another embodiment, the processor 120 may detect a rate of change (e.g., a derivative) of the measured capacitance and compare the rate of change to a threshold rate. In this embodiment, the rate of change being greater than the threshold rate may indicate that the wearable device 10 has been removed from the user's body. For example, a negative rate of change in the measured capacitance value that is greater than a defined threshold over a defined interval (see the change in the measured capacitance between time $t_2$ and $t_3$ in FIG. 7A) may be representative of the wearable device 10 being removed from the body of the user.

In yet another embodiment, the processor 120 may track a moving baseline of the measured capacitance and set threshold values as levels relative to the moving baseline which indicate whether the measured capacitance is indicative of an off-wrist event. In some embodiments, the processor 120 may track a baseline capacitance value by low-pass filtering the raw input signal received from the CDC 315. In some embodiments, the processor 120 may set an on-wrist baseline value and an off-wrist baseline value relative to the moving baseline. The processor 120 may update the on-wrist and an off-wrist baseline values in response to, for example, the average value of the moving baseline changing over time. For example, after the user has worn the wearable device 10 for a period of time, the capacitance measured by the capacitive sensor 300 may increase, thereby increasing the average of the moving baseline. The processor 120 may update the on-wrist baseline value in response to the increase in the capacitance measured by the capacitive sensor 300 to reflect this change in the measured capacitance. The average of the measured capacitance may be determined over a defined period of time.

The processor 120 may set the on-wrist baseline value as a value which is indicative of the wearable device 10 being worn by the user and may set the off-wrist baseline value as a value which is indicative of the wearable device 10 not being worn by the user. In some embodiments, the processor 120 may determine that the wearable device 10 is being worn by or otherwise on the user in response to the moving baseline being closer to the on-wrist baseline value. Similarly, the processor 120 may determine that the wearable device 10 has been removed from the user in response to the moving baseline being closer to the off-wrist baseline value. In other embodiments, the processor 120 may set threshold values corresponding to each of the on-wrist and off-wrist baseline values that are within a defined percentage deviation from the respective baseline values. The processor 120 may determine that the wearable device 10 has been removed from the user in response to determining that the moving baseline has deviated from the on-wrist baseline value by more than the defined percentage (e.g., the moving baseline has crossed the threshold value corresponding to a deviation from the on-wrist baseline value). The processor 120 may determine that the wearable device 10 is being worn by or otherwise on the user in response to determining that the moving baseline has deviated from the off-wrist baseline value by more than the defined percentage (e.g., the moving baseline has crossed the threshold value corresponding to a deviation from the off-wrist baseline value).

The processor 120 may also employ the capacitive sensor 300 to detect initial on-wrist event(s) prior to authentication of the wearable device 10 (described in further detail below). In other embodiments, the processor 120 may obtain a short-term deflection level (e.g., a change in capacitance over a defined time interval) of the input signal received from the CDC 315 by high-pass or band-pass filtering the signal and setting fixed positive and negative thresholds with which to compare the filtered signal. For example, a high-pass or band-pass filter may be used to remove or attenuate low frequency signals caused due to drift of the baseline signal and will pass the higher frequency signal caused due to changes in the proximity of the wearable device 10 to the user's body. It is noted that the band-pass filter may also remove higher frequency noise in the signal that may otherwise produce false positives. The processor 120 may then determine on-wrist or off-wrist events based on the comparison of the filtered signal with the fixed positive and negative thresholds.

FIG. 7A illustrates one example of the capacitance values that may be measured by a capacitive sensor. As discussed above, the capacitance value output from the CDC 315 may vary due to factors other than the wearable device 10 being removed from the user, such as, for example, due to variations in temperature/climate or movement of the sensor electrode 310 with respect to the user due to natural movement the wearable device 10 during operation (e.g., movement of the user's wrist may cause the wearable device 10 to move further away or closer to the user's wrist due to momentum of the wearable device 10). Examples of such changes in capacitance are depicted as the changes in the measured capacitance before time $t_5$ and after time $t_6$ in FIG. 7A.

Between times $t_5$ and $t_6$ of FIG. 7A, the measured capacitance may have a relatively large drop in value due to the wearable device 10 being removed from the user. The processor 120 may be configured to detect the change in measured capacitance between times $t_5$ and $t_6$ as indicating that the wearable device 10 has been removed from the user, and also to detect that the change in measured capacitance at other times (e.g., between times $t_2$ and $t_3$) as not indicating that the wearable device 10 has been removed from the user, by comparing changes in the measured capacitance over a defined time period. For example, the change in measured capacitance between the peak at time $t_1$ and the trough at time $t_4$ may in some cases have a magnitude that is similar to the change in measured capacitance associated with an off-wrist event (e.g., between times $t_5$ and $t_6$). However, since the change in measured capacitance between the peak at time $t_1$ and trough at time $t_4$ is over a greater period of time than the defined time period (e.g., the time period between $t_2$ and $t_3$ and the time period between $t_5$ and $t_6$) the processor 120 may be able to distinguish this change in capacitance from a change in capacitance that is indicative of an off-wrist event (e.g., the wearable device 10 being removed from the user).

In contrast, the change in measured capacitance between times $t_5$ and $t_6$ may be greater than a threshold change within the defined interval. Since the change in measured capacitance between times $t_5$ and $t_6$ is within the defined time interval, the processor 120 may be able to determine that this change in measured capacitance is indicative of the wearable device 10 being removed from the user.

FIG. 7B illustrates another example of the capacitance values that may be measured by the capacitive sensor. In this example, the off-wrist event may occur near a peak in the measured capacitance value. As such, the measured capacitance values from times $t_3'$ to $t_4'$ may not fall below the trough at time $t_2'$. As such, in the example of FIG. 7B, a simple threshold capacitance value (in contrast to a change in the measured capacitance within a defined interval) may not accurately indicate whether the wearable device 10 has been removed from the user since such a threshold capacitance value would not be able to distinguish between the trough at time $t_2'$ and the capacitance value at time $t_4'$.

Optical Sensor

The processor 120 in conjunction with the capacitive sensor 300 (e.g., as illustrated in FIG. 1B) may reliably detect the presence of a conductive object close to the sensor electrode; however, the processor 120 may not be able to easily distinguish between a human body and an inanimate object (e.g., a metal desk). Accordingly, in certain embodiments, an optical sensor 500 such as a PPG sensor 500 may be utilized to supplement the measurements provided by the capacitive sensor 300. The term "optical sensor" may be used interchangeably with PPG sensor hereinafter; however, in certain embodiments, the optical sensor may comprise a non-PPG sensor. For example, the optical sensor 500 may function as a proximity sensor that measures proximity to an object such as a reflective surface (e.g., a user's wrist) based on the luminance and/or amplitude of reflected light from the object.

In one example, the PPG sensor 500 may detect a cardiac signal that may be indicative of the measured capacitance being due to the presence of a human body (rather than an inanimate object, for example). The processor 120 may be configured to determine that when the measured capacitance is indicative of a conductive object being proximate to the capacitive sensor electrode 310 and the cardiac signal is present in the output from the PPG sensor 500, a human is wearing the wearable device 10. The use of a PPG sensor 500 for identifying a cardiac signal (e.g., in connection with heart rate monitoring) is well understood by those skilled in the art, and will not be described in greater detail herein. In some embodiments, the processor 120 may utilize a heart rate tracking algorithm in connection with a heart rate monitoring function of the PPG sensor 500 to provide further confidence about whether the wearable device 10 is on or off wrist (e.g., by confirming that a heart rate sampled based on output from the PPG sensor 500 is within an expected heart rate range).

Figure 8:
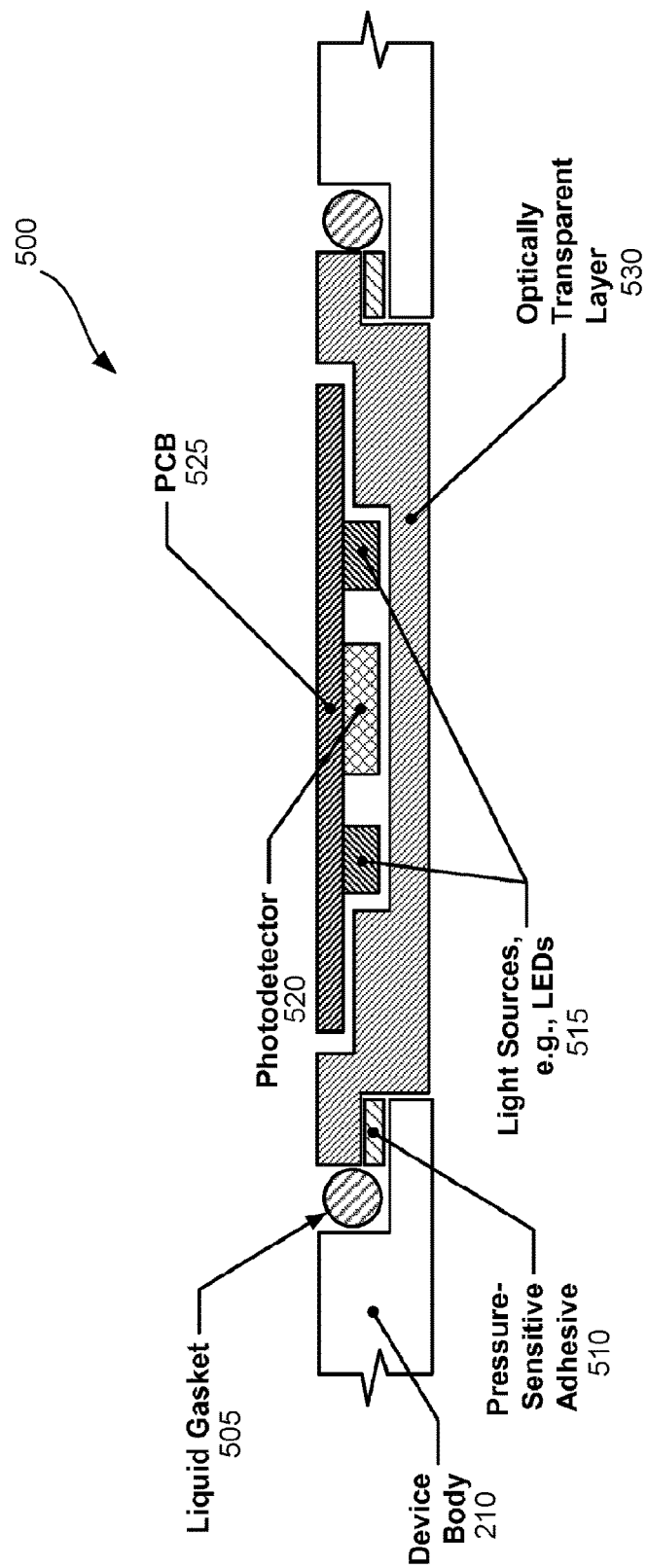
FIG. 8 is a cross-sectional view of an example wearable device that includes an optical sensor in accordance with aspects of this disclosure.

FIG. 8 is a cross-sectional view of a portion of a wearable device that includes an optical sensor in accordance with aspects of this disclosure. In the embodiment of FIG. 8, the optical sensor 500 may be implemented as a PPG sensor 500. The PPG sensor 500 may be formed within the device body 210 and may include one or more light sources (e.g., LEDs) 515, a photodetector 520, a PCB 525, and an optically transparent layer 530. The optically transparent layer 530 may be attached to the device body 210 via a pressure-sensitive adhesive 510 and a liquid gasket 505 may be provided to seal the wearable device 10.

In the embodiment of FIG. 8, the two light sources 515 may be placed on either side of the photodetector 520 to facilitate PPG sensing. The number of light sources 515 may vary in other implementations. Depending on the embodiment, the light sources 515 may emit green light, infrared light, or light having multiple wavelengths (e.g., red, green, and infrared light or any combination thereof). In certain embodiments, a light-blocking material (not illustrated) may be placed between the light sources 515 and the photodetector 520 to prevent any light from the light sources 515 from reaching the photodetector 520 without first exiting the body of the wearable device 10. An optically transparent layer 530 may be placed on the lower surface of the PPG sensor 500 to form a seal. Although the optically transparent layer 530 is illustrated as being flush with the device body 210, in other embodiments, the optically transparent layer 530 may form a protrusion as shown in FIG. 3. The optically transparent layer 530 may serve other functions such as preventing liquid or debris from entering the wearable device 10 where the light source(s) 515 or the photo-detector(s) 520 are placed. The optically transparent layer 530 may be formed through in-mold labeling (IML). The light source(s) 515 and the photodetector(s) 520 may be placed on the PCB 525, which may be flexible in certain embodiments.

The configuration of FIG. 8 may improve the efficiency of light flux coupling between the components of the optical sensor 500 and the user's body. For example, in one embodiment, the light source(s) 515 and/or the associated detector(s) 520 may be disposed on a flexible or pliable substrate, such as PCB 525, that may flex, allowing the skin-side of the wearable device 10, which may be made from a compliant material, to conform (e.g., without additional processing) or be capable of being shaped (or compliant) to conform to the shape of the body part (e.g., the user's wrist, arm, ankle, and/or leg) to which the wearable device 10 is coupled to or attached during normal operation so that the light source(s) 515 and/or the associated detector(s) 520 is/are close to the skin of the user (e.g., with little to no gap between the skin-side of the device and the adjacent surface of the skin of the user).

In one embodiment, the light source(s) 515 and/or the associated detector(s) 520 may be disposed on a Flat Flex Cable (FFC) or flexible PCB 525. In one aspect, the flexible or pliable substrate (e.g., an FFC or flexible PCB 525) may connect to a second substrate (e.g., PCB) within the device having other components disposed thereon (e.g., the data processing circuitry). Optical components of differing heights may be mounted to different portions or protrusions of flexible substrate and pressed or secured to the housing surface such that the optical components are flush to the housing surface. In another aspect, the second substrate may be a relatively inflexible or non-pliable substrate, fixed within the device, having other circuitry and/or component(s) (passive and/or active) disposed thereon.

In related aspects, the processor 120 of the wearable device 10 (e.g., illustrated in FIGS. 1A, 1B and 6) may calibrate the optical sensor 500 based on the output of the optical sensor 500. For example, the processor 120 may determine at least one characteristic of the user's skin (e.g., the user's skin color) based on the output of the optical sensor 500. The processor 120 may calibrate an expected amount of light to be received by the photodetector 520 based on the characteristic(s) of the user's skin. For instance, a user with darker skin tone will be associated with a greater absorption of green light as measured from an emitter to a detector of an optical (e.g., PPG) sensor when the sensor is positioned close to the user's skin. Thus, detection of "on" and "off" wrist events may then be calibrated relative to the user's skin color response to the optical sensor.

In further related aspects, the PPG circuitry may include amplification circuitry optimized to obtain quality signals regardless of environmental conditions including, but not limited to, motion, ambient light, and skin color. Two examples of such PPG amplification circuitry are described in connection with FIGS. 9A and 9B.

Figure 9A:
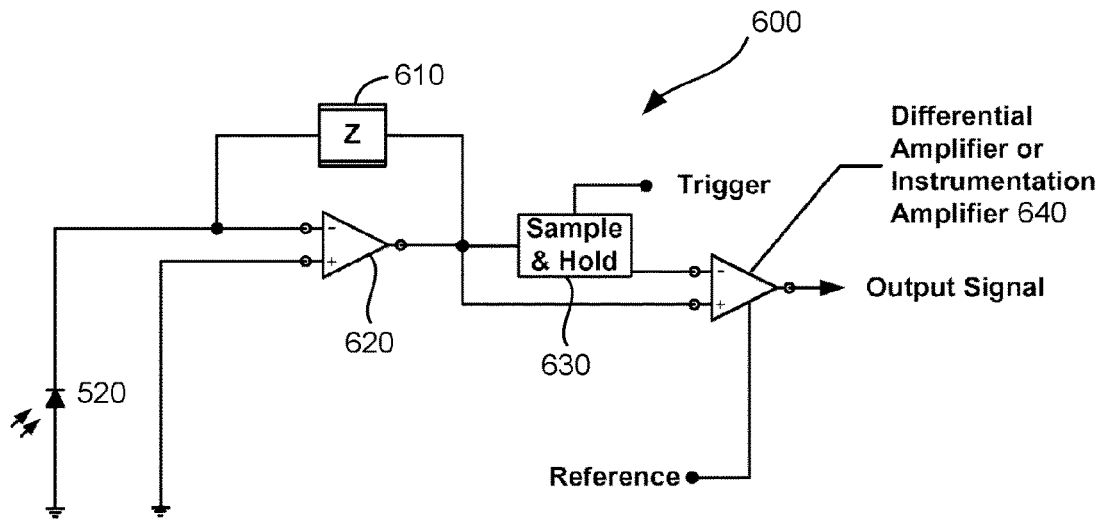
FIGS. 9A and 9B are example schematics of circuits used for a photoplethysmographic (PPG) sensor in accordance with aspects of this disclosure.

FIG. 9A illustrates an example schematic of a sample-and-hold circuit and differential/instrumentation amplifier which may be used in PPG sensing. The example circuitry 600 of FIG. 9A may include a photodetector 520, a feedback reactance 610, an amplifier 620 (e.g., a differential amplifier), a sample-and-hold circuit 630 (e.g., a buffer), and a differential or instrumental amplifier 640. The output of the photodetector 520 may be connected to first input of the amplifier 620 (e.g., the negative terminal) to be compared with a ground signal (or another signal) connected to a second input of the amplifier 620 (e.g., the positive terminal). The output of the amplifier 620 may be connected to the same input (e.g., the first input) of the amplifier as the photodetector 520. The output of the amplifier may also be connected to the sample-and-hold circuit 630 and a first input of the differential/instrumentation amplifier 640 (e.g., the positive terminal). The output of the sample-and-hold circuit 630 may also be connected to a second input of the differential/instrumental amplifier 640 (e.g., the negative terminal). The differential/instrumental amplifier 640 may then output a comparison between the amplified photodetector 520 output and a previously sampled amplified photodetector 520 output. The output signal from the circuit 600 may therefore be an amplified difference between a current sample and a previous sample of the photodetector 520, referenced to a given voltage.

Figure 9B:
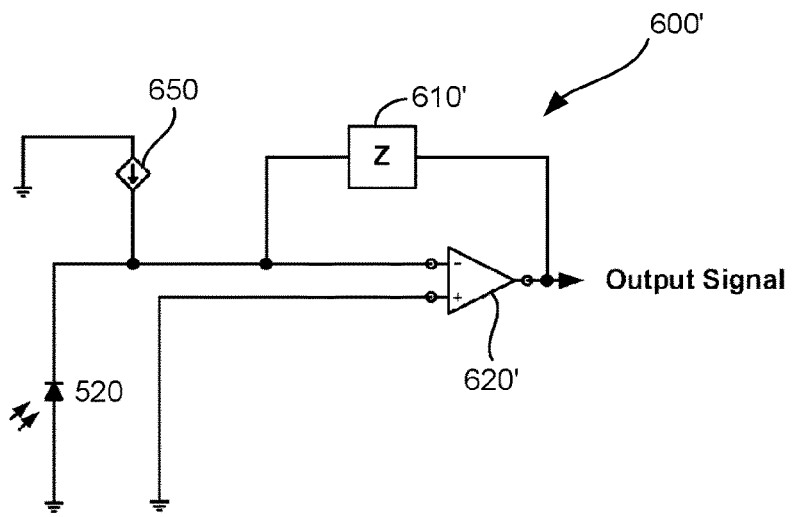

FIG. 9B illustrates an example schematic of a circuit for a PPG sensor using a controlled current source to offset "bias" current prior to a transimpedance amplifier. The circuit 600' of FIG. 9B may include a photodetector 520, a current source 650, a feedback impedance 610', and an amplifier 620' (e.g., a differential amplifier). The output of the photodetector 520 may be combined with the output of the current source 650 and then supplied to a first input of the amplifier 620' (e.g., the negative terminal). A second input of the amplifier 620' (e.g., the positive terminal) may be connected to ground or another potential. The output signal from the amplifier 620' may be fed back to the first input of the amplifier 620' connected to the photodetector 520 via the loop with the feedback impedance 610'. This arrangement of circuit components may allow for a greater gain to be applied at the transimpedance amplifier stage.

Example Flowchart for Determining Occurrence of Off-Wrist Event

An optical sensor configured for off-wrist detection, such as the PPG sensor 500 described herein, may be designed to detect the proximity and cardiac content in the vicinity of the optical sensor 500 to detect a human wrist. However, in certain circumstances the optical sensor 500 may not be able to easily distinguish between a cardiac signal and an inanimate object that is in relative motion to the optical sensor 500 when the motion contains frequencies within the range of heart rate. For example, when the optical sensor 500 is placed into a bag or pocket of a walking subject, the processor 120 may mistake the output of the optical sensor 500 due to the motion of the bag or clothing fabric as a cardiac signal. Accordingly, in at least one embodiment, the outputs from a capacitive sensor 300 and an optical sensor 500 may be considered and/or combined to provide a more accurate detection of an off-wrist event by determining whether the object being sensed is conductive (e.g., a human body) or not conductive (e.g., a thin fabric).

Figure 10:
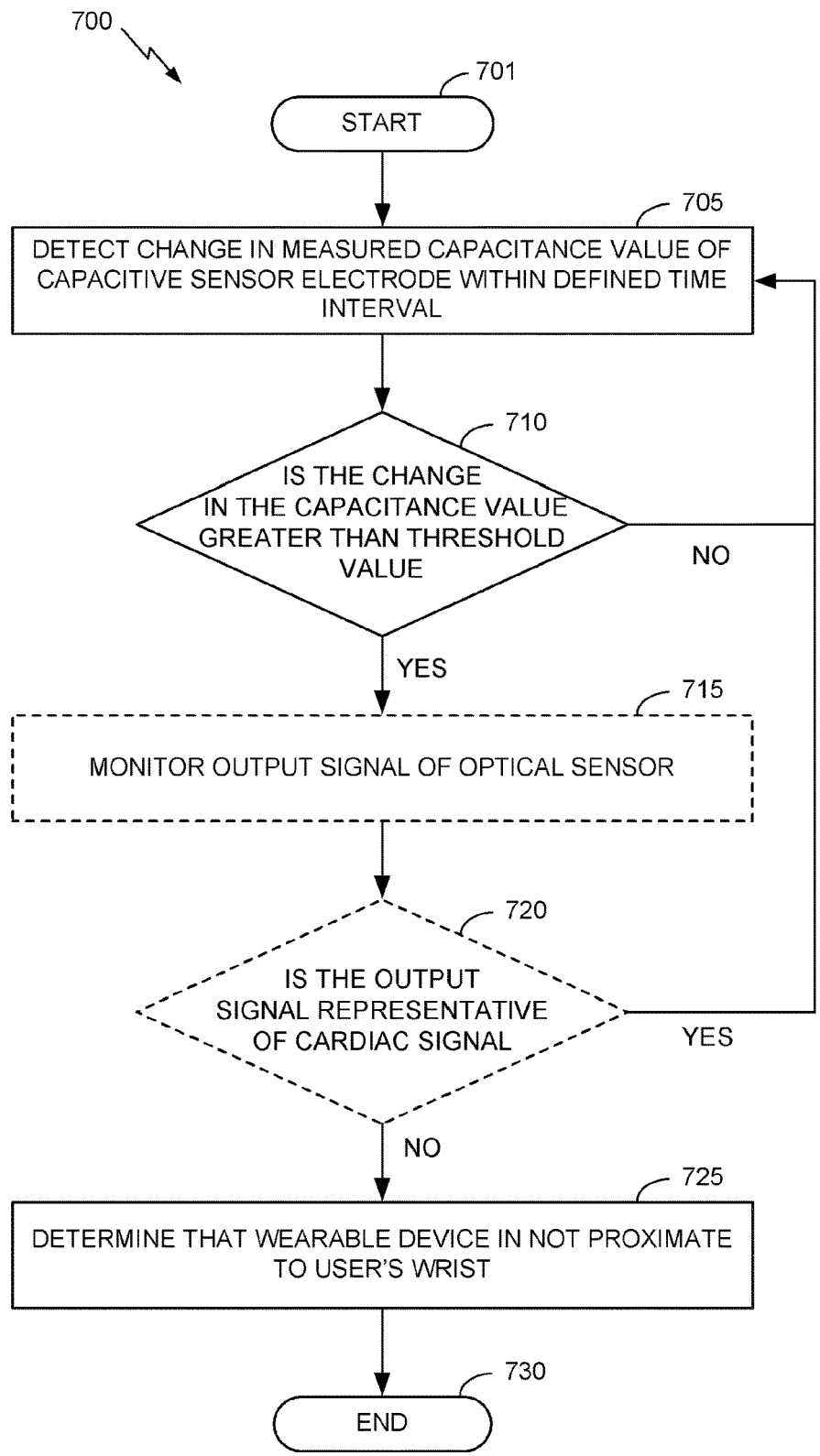
FIG. 10 is a flowchart illustrating an example method for off-body detection in accordance with aspects of this disclosure.

FIG. 10 is a flowchart illustrating an example method operable by a wearable device 10, or component(s) thereof, for off-body detection in accordance with aspects of this disclosure. For example, the steps of method 700 illustrated in FIG. 10 may be performed by a processor 120 of the wearable device 10 or an entity in communication with the wearable device. For example, the wearable device 10 may be in communication with a client device 20 (e.g., mobile phone, etc.) which can perform the method 700 or portions thereof. For convenience, method 700 is described as performed by the processor 120 of the wearable device 10.

The method 700 begins at block 701. At block 705, the processor 120 may detect a change (e.g., a change in a magnitude) of a measured capacitance value of a capacitive sensor electrode within a defined time interval. The defined time interval may be selected based on the time scale associated with removing a wearable device from a wrist. The time interval may be short enough such that variations in the measured capacitance due to variables other than off-wrist events (e.g., changes in temperature) measured within the time interval are less than a threshold change which is associated with off-wrist events measured within the time interval.

At block 710, the processor 120 may determine whether the change in the measured capacitance value is greater than a threshold change. When the change in the measured capacitance value is not greater than the threshold change, the measured change may not be indicative of an off-wrist event and the method 700 returns to block 705. When the change in the measured capacitance value is greater than the threshold change, the change in capacitance may be indicative of an off-wrist event, e.g., may be a potential off-wrist event, and the method 700 proceeds to block 715.

At block 715, the processor 120 may perform the optional step of monitoring an output signal of an optical sensor 500. For example, the processor 120 may monitor, based on output of the optical sensor 500, at least one characteristic of a heartbeat waveform of a user of the wearable device 10. In particular, by analyzing output from the optical sensor 500, the processor 120 may be able to verify whether the output from the optical sensor 500 is consistent with the detected potential off-wrist event. The method 700 then proceeds to optional step 720, at which the processor 120 may determine whether the output signal of the optical sensor 500 is representative of a cardiac signal. For example, the processor 120 may determine that the at least one characteristic of the user's heartbeat waveform is not representative of a cardiac signal. When the output signal of the optical sensor 500 is representative of a cardiac signal, the processor may determine that the potential off-wrist event was not accurate, and the method 700 returns to step 705. When the output signal of the optical sensor 500 is not representative of a cardiac signal, the processor 120 may determine that the potential off-wrist event was accurate and the method 700 proceeds to block 725. For example, the processor 120 may determine that the wearable device has been removed from the user in response to determining that the at least one characteristic of the user's heartbeat waveform is not representative of a cardiac signal. At block 725, the processor 120 determines that the wearable device 10 is not proximate to a user's wrist, e.g., that the wearable device has been removed from a user. The method ends at block 730.

Although the method 700 of FIG. 10 was described as first analyzing the capacitive sensor 300 output and then confirming an off-wrist event by analyzing the output of the optical sensor 500, the method 700 may be performed in the reverse order. For example, the method 700 may first perform steps 715 and 720 before steps 705, 710, and 725. For example, if the processor 120 determines that the output signal of the optical sensor 500 is not representative of a cardiac signal (see step 720), then this may be indicative of an off-wrist event. The processor may then proceed to perform steps 705 and 710, and if the processor determines that a change in the measured capacitance value is greater than a threshold change (see step 710), then the processor 120 may determine that the off-wrist event did occur, and the wearable device 10 is not proximate to a user's wrist (see step 725). Additionally, in some embodiments, the optical sensor 500 may be turned off or in a power conservation mode. In these embodiments, the optical sensor 500 may remain in the off or power conservation mode until the capacitive sensor identifies a potential off-wrist event (e.g., as described in steps 705 and 710). Thereafter, the optical sensor 500 may be engaged to verify the accuracy of the potential off-wrist event (e.g., as described in steps 715, 720, and 725). In embodiments where the optical sensor 500 output is analyzed prior to the capacitive sensor 300, the capacitive sensor may be turned off or in a power conservation mode (e.g., until the output signal of the optical sensor 500 is not representative of a cardiac signal and therefore indicates a potential off-wrist event, at which point the capacitive sensor 300 may be powered on). The output from additional sensors may also be analyzed when detecting off-wrist events. For example, the output of an accelerometer may be used by the processor 120 in analyzing the output of the optical sensor 500 and/or the capacitive sensor 300.

In some embodiments, the processor 120 detects an off-wrist event by analyzing output from the optical sensor 500 alone, without regard to capacitive sensor readings. For example, steps 705 and 710 may be omitted from method 700 in FIG. 10. Thus, in some embodiments, the processor 120 may monitor an output signal of the optical sensor 500 (step 715), and if the processor 120 determines that the output signal of the optical sensor 500 is not representative of a cardiac signal (step 720), then processor 120 may determine that the wearable device 10 is not proximate to the user's wrist (block 725).

Although not illustrated in FIG. 10, in some embodiments, the processor 120 may also optionally detect whether the output signal of the optical sensor 500 falls to or below an optical threshold indicative of the wearable device 10 not being proximate to the user's skin, consistent with various techniques described herein. For example, in some embodiments, this optional step may occur between steps 715 and 720 or between steps 720 and 725 in the method 700. Thus, in some embodiments, the processor 120 may determine that the wearable device 10 is not proximate to the user's wrist (see step 725), in response to (i) the change in the measured capacitance value of the capacitive sensor electrode within the defined time interval being greater than the threshold change (see step 710), (ii) the output signal of the optical sensor 500 not being representative of a cardiac signal (see step 720), and/or (iii) the output signal of the optical sensor 500 falling to or below an optical threshold indicative of the wearable device 10 not being proximate to the user's skin, or any combination of (i), (ii), and (iii).

In other embodiments, the processor 120 may also verify the accuracy of biometric data output from one or more of the biometric sensors (e.g., the biometric sensor(s) 160 shown in FIG. 1A) after the wearable device 10 has been determined to have been removed from a user. For example, after the wearable device 10 has been determined to have been removed from a user, the processor 120 may set a flag associated with output received after the detected removal from one or more of the biometric sensors 160. This flag may indicate that the output received from the associated one or more biometric sensors 160 should be verified for accuracy. The accuracy of the output received from the one or more biometric sensors 160 may then be verified by the processor 120 (and/or the client device 20 and/or the server 22).

In some implementations, the processor 120 may determine an on-wrist confidence metric for the measurements associated with each of the capacitive sensor 300, the optical sensor 500, and/or other biometric sensors 164, where each confidence metric indicates a level of confidence or trustworthiness in the accuracy of the measurements associated with each of the sensors. A first on-wrist confidence metric, determined based on output of the capacitive sensor 300, and a second on-wrist confidence metric, determined based on output of the optical sensor 500, may be used by the processor 120 to determine whether to use the output of the capacitive sensor 300 or the output of the optical sensor 500 in determining that the wearable device 10 has been removed from the user. For example, the processor 120 may determine a first on-wrist confidence metric based on the output of the capacitive sensor and determine a second on-wrist confidence metric based on the output of the optical sensor. The processor 120 may classify one of the first on-wrist confidence metric and the second on-wrist confidence metric as a greater value confidence metric and select one of the capacitive sensor and the optical sensor associated with the greater confidence metric. Thus, the processor 120 may determine that the wearable device has been removed from the user based on the output of the selected sensor. The first and second on-wrist confidence metrics may be determined based on, for example, noise in the corresponding sensor outputs, unexpected patterns in the corresponding sensor outputs, etc.

Applications for the Determination of Off-Wrist Event

As discussed above, the determination that the wearable device 10 has been removed from the body of a user may be used to de-authenticate the user from the wearable device 10. There are a number of applications in which the wearable device 10 may use the determination that the wearable device 10 has been removed from the user. One application of the authentication and de-authentication of the wearable device 10 is to add security to the use of the wearable device 10 in the context of financial transactions. However, the wearable device 10 may be used for a number of other transactions or tasks. For example, while the wearable device 10 is authenticated, the user may use the wearable device 10 for one or more secure transactions or tasks, including but not limited to monetary transfer, credit card purchase(s), automated teller machine (ATM) cash withdrawal or transaction, ATM authentication, keyless entry into a vehicle, keyless starting of a vehicle, keyless entry through a door, opening of a lock, execution of an electronic signature (e-signature), unlocking of a computer, automatic logging into a web account or website, "friending" someone in a social network or exchange of social network information (e.g., Fitbit®, Facebook®, LinkedIn®), exchange of contact information, disabling or disarming of a home or business security system, automatic upload of biometric data to an online user account associated with the user, and/or altering the preferences on a thermostat. These examples of transactions or tasks may be performed by near contact (e.g., NFC) or direct contact with objects (e.g., the user may touch a door) or by launching an application on the wearable device 10 that transmits a signal to the object(s) either directly (peer-to-peer) or indirectly (client-server via Internet).

The de-authentication or de-authorization of the wearable device 10 from performing secure transactions (e.g., monetary transfer, credit card purchase(s), ATM cash withdrawal or transaction, ATM authentication, etc.) may be performed by the processor 120 in accordance with an NFC standard for the de-authorization of financial transactions. This may include, for example, the processor 120 powering off an NFC chip of the wearable device 10. When the NFC chip is powered down, other devices such as NFC readers are unable to scan or read information from the NFC chip, and thus, are unable to access information that may be stored on the NFC chip such as, for example, credit card, debit card, and/or bank account information. The processor 120 may power up the NFC chip after the wearable device 10 has been re-authenticated by an authorized user of the wearable device 10. In related aspects, the wearable device 10 may employ any other technique known to those skilled in the art for the de-authorization of financial transactions performed with the NFC chip and/or the wireless transceiver 140 of the wearable device 10.

In one example, a user may be authenticated with a wearable device 10 when first putting on a wearable device 10 via inputting a pin or using a biometric identification method. In another example, the user may be asked to authenticate the wearable device 10 at the time of the first secure transaction or task after putting on the wearable device 10. In yet another example, the wearable device may be paired to a client device 20 (e.g., mobile phone). When the user first wears the wearable device 10, the user may be asked to authenticate the wearable device 10 via the client device 20 with a pin, fingerprint, or other biometric data (e.g., heart rate signature). Authentication may also be performed from the client device 20 via, for example, a fingerprint sensor, facial recognition, pin entry, password entry, or pattern matching (e.g., swipe pattern). Thereafter, for the duration of the wearable being on the user's wrist as determined by the processor 120 based on measurements from the capacitive sensor 300 and/or the optical sensor 500 via the techniques disclosed herein, the user may be authenticated. Once the wearable device 10 is removed and determined to have been removed from the user based on the measurements from the capacitive sensor 300 and/or the optical sensor 500 via the disclosed techniques, the user may be de-authenticated from the wearable device 10.

In one example, the wearable device 10 may become de-authenticated if it is not in close proximity to a client device 20 (e.g., mobile phone) for a specified period of time. For instance, if the wearable device 10 is not within the Bluetooth range of the client device 20 for 10 minutes, the wearable device 10 may be de-authenticated regardless of whether the processor 120 has detected an off-wrist event. In another example, the wearable device 10 may become de-authenticated when the wearable device 10 is turned off.

The off-wrist detection methods disclosed herein may be used to ensure that the user has not taken off the wearable device 10, since removal of the wearable device 10 from the user's body is detectable as an off-wrist event using the techniques described herein. Once the wearable device 10 has determined that the wearable device 10 has been removed from the user, the wearable device 10 may be de-authenticated, thereby requiring the user to re-authorize the wearable device 10 to engage in any activities that require authentication. This authorization technique may be used, for example, to authorize payments via the wearable device 10 when paired to a credit/debit card. A similar technique may be used for authorization of other sensitive tasks, such as entry into locked doors, password access to computers, pin entry for unlocking a phone, etc. These techniques may also be used for wearable devices 10 which are shared between multiple users, allowing the processor 120 to switch between modes of operation depending on the particular user who is wearing the wearable device 10. This may also allow biometric data to be correctly associated with the particular user that was wearing the wearable device 10 when such data was observed.

In one implementation, the determination of whether the wearable device has been removed from the user may be used to determine when to measure other biometric signals (e.g., heart rate, heart rate variability, blood oxygenation, body temperature, galvanic skin response, etc.) or when to end various operations of the wearable device 10, thereby optimizing power draw. For example, certain biometric sensors 160 (including but not limited to the optical sensor 500) may be turned off or put into a power conservation mode when the wearable device 10 has been removed from the user. Further, the accuracy of the algorithms for analyzing output from the biometric sensors 160 may degrade when invalid data (such as biometric sensor 160 measurements taken when the device is not worn by the user) is included in the analysis. Therefore, by accurately detecting off-wrist events, these types of spurious data measurements may be prevented from being processed or considered by an algorithm or from being introduced into a user's records. The analysis of the data from the biometric sensors 160 may also be used to increase confidence in the on-wrist and off-wrist state in certain implementations. For example, the biometric sensors 160 may provide measurements of skin temperature (e.g., via a skin temperature thermometer), galvanic skin response (e.g., from a galvanic skin response sensor), electromyography (e.g., from an electromyographic sensor), motion (e.g., the user registers enough movement in a time window as measured by an accelerometer), etc., one or more of which may be incorporated into the determination of whether the wearable device 10 has been removed from the user.

In another implementation, the determination of whether the wearable device 10 has been removed from the user may be used to customize the collection and/or analysis of biometric data for the user. The techniques disclosed herein may also be used to track a user's on-wrist and off-wrist states over a period of time and send this information, along with other collected biometric data to an Internet-connected server (e.g., the server 22). The collected on-wrist and off-wrist information may be used by the Internet-connected server or associated processing infrastructure to improve the accuracy of algorithms used to analyze biometric data received from the biometric sensor(s) 160 to calculate metrics, including but not limited to resting heart rate, caloric expenditure, fitness level, etc. The tracked on-wrist and off-wrist state periods may also be used within the Internet-connected server to calculate statistics which track user engagement of the product (the wearable device 10), including but not limited to how often or when he/she is wearing the wearable device 10. This information may be used to tailor specific information (e.g., fitness related updates, marketing, etc.) to each user to increase his/her engagement with the wearable device 10 and/or associated services. This information may also be presented to the user so that he/she can track his/her engagement with the wearable device 10 and/or associated services.

In some implementations, the wearable device 10 may be shared between a plurality of users and may be configured to track biometric data for each of the users and/or automatically upload the biometric data for each of the users to online user accounts associated with each of the users. Accordingly, in order to associate measured biometric data with the particular users who generated the data, each of the users may be authenticated with the wearable device 10 upon putting on the wearable device 10. After the wearable device 10 detects an off-wrist event, the wearable device 10 may de-authenticate the corresponding user such that biometric data generated thereafter is not associated with the corresponding user. The wearable device 10 may then prevent further automatic uploading of biometric data to an online user account associated with the user until the user is re-authenticated with the wearable device 10.

Further Example Flowcharts for Determining Off-Wrist Event

Figure 11:
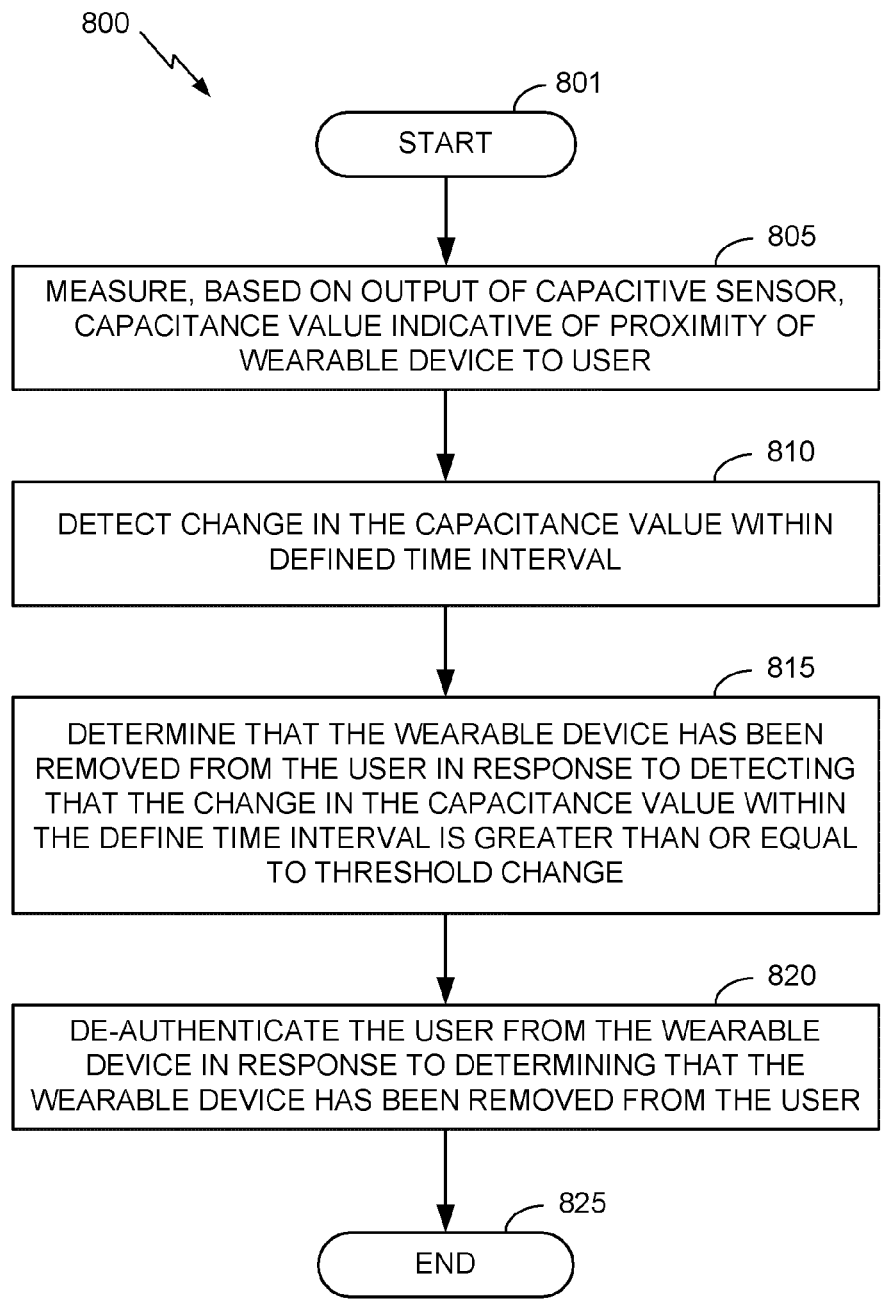
FIG. 11 is a flowchart illustrating another example method for off-body detection in accordance with aspects of this disclosure.

FIG. 11 is a flowchart illustrating another example method operable by a wearable device 10, or component(s) thereof, for off-wrist detection in accordance with aspects of this disclosure. For example, the steps of method 800 illustrated in FIG. 11 may be performed by a processor 120 of the wearable device 10. In another example, a client device 20 (e.g., a mobile phone) in communication with the wearable device 10 may perform at least some of the steps of the method 800. For convenience, the method 800 is described as performed by the processor 120 of the wearable device 10.

In one implementation, the wearable device 10 comprises one or more biometric sensors 160 including a capacitive sensor 300 and the processor 120. The method 800 begins at block 801. At block 805, the processor 120 measures, based on output of the capacitive sensor 300, a capacitance value indicative of proximity of the wearable device 10 to a user. At block 810, the processor 120 detects a change in the capacitance value within a defined time interval. When the change is greater than or equal to a threshold change, the change may be indicative of the wearable device 10 not being proximate to the user's skin. At block 815, the processor 120 determines that the wearable device 10 has been removed from the user. The processor 120 may determine that the wearable device 10 has been removed from the user in response to detecting that the change in the capacitance value within the defined time interval is greater than or equal to the threshold change. At block 820, the processor 120 de-authenticates the user from the wearable device 10 in response to determining that the wearable device 10 has been removed from the user. The method 800 ends at block 825.

Figure 12:
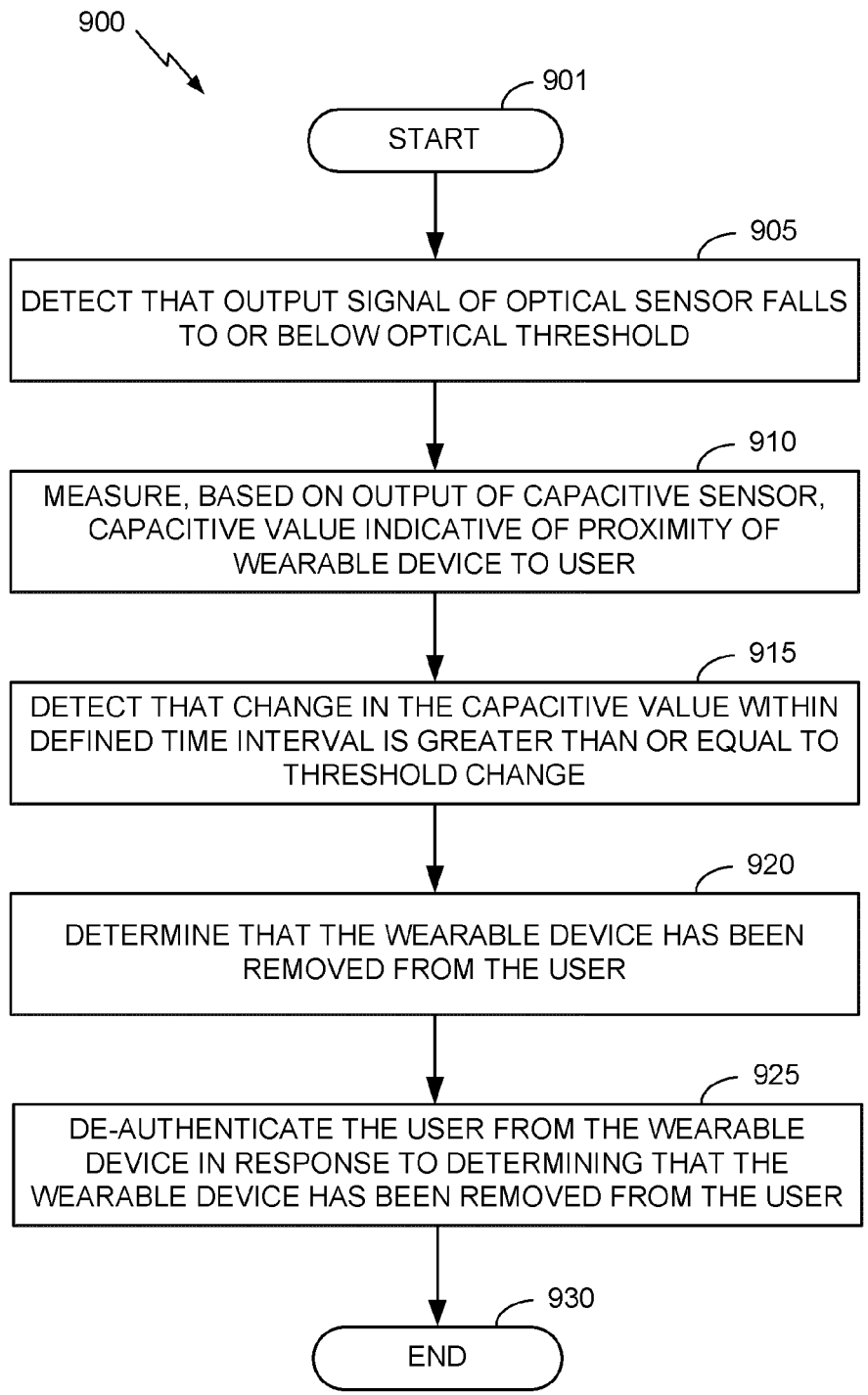
FIG. 12 is a flowchart illustrating yet another example method for off-body detection in accordance with aspects of this disclosure.

FIG. 12 is a flowchart illustrating yet another example method for off-wrist detection in accordance with aspects of this disclosure. The steps illustrated in FIG. 12 may be performed by a wearable device 10 or component(s) thereof. For example, the method 900 may be performed by a processor 120 of the wearable device 10. In another example, a client device 20 in communication with the wearable device 10 may perform at least some of the steps of the method 900. For convenience, the method 900 is described as performed by the processor 120 of the wearable device 10.

In one implementation, the wearable device 10 comprises an optical sensor 500, a capacitive sensor 300, and a processor 120. The method 900 begins at block 901. At block 905, the processor 120 detects that an output signal of the optical sensor 500 falls to or below an optical threshold indicative of the wearable device 10 not being proximate to the user's skin. At block 910, the processor 120 measures, based on output of the capacitive sensor 300, a capacitance value indicative of proximity of the wearable device 10 to the user. At block 915, the processor 120 detects that a change in the capacitance value within a defined time interval is greater than or equal to a threshold change indicative of the wearable device 10 not being proximate to the user's skin. At block 920, the processor 120 determines that the wearable device 10 has been removed from the user. The processor 120 may determine that the wearable device 10 has been removed from the user in response to at least one of (i) detecting that the output signal of the optical sensor 500 has fallen to or below the optical threshold and (ii) detecting that the change in the capacitance value within the defined time interval is greater than or equal to the threshold change. At block 925, the processor 120 de-authenticates the user from the wearable device 10 in response to determining that the wearable device 10 has been removed from the user. The method 900 ends at block 930.

Although not illustrated in FIG. 12, in some embodiments, the processor 120 may also optionally detect whether the output signal of the optical sensor 500 is representative of a cardiac signal, consistent with various techniques described herein. For example, in some embodiments, this optional step may occur before step 920 in the method 900. Thus, in some embodiments, the processor 120 may determine that the wearable device 10 has been removed from the user (see step 920), in response to (i) the output signal of the optical sensor 500 falling to or below an optical threshold indicative of the wearable device 10 not being proximate to the user's skin (see step 905), (ii) the change in the capacitance value within the defined time interval being greater than or equal to the threshold change indicative of the wearable device 10 not being proximate to the user's skin (see step 915), and/or (iii) the output signal of the optical sensor 500 not being representative of a cardiac signal, or any combination of (i), (ii), and (iii).

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure. However, the combinations of features between the respective embodiments are not necessarily limited thereto. Various embodiments of the disclosure have been described. These and other embodiments are within the scope of the following claims.

What is claimed is:

1. A method of operating a wearable device, the wearable device comprising one or more biometric sensors including a capacitive sensor, the method comprising:
   attenuating, via a filter, defined frequencies in an output signal of the capacitive sensor;
   determining, based at least on the output signal, a capacitance value indicative of a distance of the wearable device to a user, the capacitive sensor comprising a capacitive sensor electrode and being configured to generate the capacitance value based on the distance between the capacitive sensor electrode and the user;
   determining a change in the capacitance value within a defined time interval, the change being greater than or equal to a threshold change indicative of the wearable device not being proximate to the user's skin;
   determining that the wearable device has been removed from the user in response to detecting that the change in the capacitance value within the defined time interval is greater than or equal to the threshold change; and
   de-authenticating the user from the wearable device in response to determining that the wearable device has been removed from the user.

2. The method of claim 1, wherein the de-authenticating of the user from the wearable device comprises de-authorizing mobile payment with the wearable device.

3. The method of claim 1, wherein the de-authenticating of the user from the wearable device comprises de-authorizing at least one of: automated teller machine (ATM) transactions; keyless entry into a vehicle; keyless starting of a vehicle; keyless entry through a door; opening of a lock; execution of an electronic signature; unlocking of a computer; automatic logging into a website; exchange of social network information; exchange of contact information; disarming of a security system; automatic upload of biometric data to an online user account associated with the user; and altering of preferences of a thermostat.

4. The method of claim 1, wherein the wearable device further comprises an optical sensor, the method further comprising:
monitoring, based on output of the optical sensor, at least one characteristic of the user's heartbeat waveform.

5. The method of claim 4, further comprising:
determining a first on-wrist confidence metric based on the output of the capacitive sensor;
determining a second on-wrist confidence metric based on the output of the optical sensor;
classifying one of the first on-wrist confidence metric and the second on-wrist confidence metric as a greater value confidence metric; and
selecting one of the capacitive sensor and the optical sensor associated with the greater confidence metric,
wherein the determining that the wearable device has been removed from the user is performed based on the output of the selected sensor.

6. The method of claim 4, further comprising:
determining that the at least one characteristic of the user's heartbeat waveform is not representative of a cardiac signal,
wherein the determining that the wearable device has been removed from the user is further in response to determining that the at least one characteristic of the user's heartbeat waveform is not representative of a cardiac signal.

7. The method of claim 6, wherein the determining that the at least one characteristic of the user's heartbeat waveform is not representative of a cardiac signal is performed in response to determining that the change in the capacitance value within the defined time interval is greater than or equal to the threshold change.

8. The method of claim 6, wherein the determining that the change in the capacitance value within the defined time interval is greater than or equal to the threshold change is performed in response to determining that the at least one characteristic of the user's heartbeat waveform is not representative of a cardiac signal.

9. The method of claim 4, further comprising:
determining, based on the output of the optical sensor, at least one characteristic of the user's skin; and
calibrating, based on the determined at least one characteristic of the user's skin, an expected amount of light to be received by the optical sensor during the operating of the optical sensor,
wherein the monitoring of the at least one characteristic of the user's heartbeat waveform is performed in response to the calibrating.

10. The method of claim 4, wherein the optical sensor comprises a photoplethysmographic (PPG) sensor.

11. The method of claim 1, wherein the wearable device further comprises an optical sensor, the method further comprising:
detecting that an output signal of the optical sensor falls to or below an optical threshold indicative of the wearable device not being proximate to the user's skin,
wherein the determining that the wearable device has been removed from the user is further in response to detecting that the output signal of the optical sensor has fallen to or below the optical threshold.

12. The method of claim 1, further comprising authenticating the user with the wearable device in response to receiving from the user at least one of: a personal identification number (PIN); a fingerprint; biometric data; facial recognition; a password; and a pattern match.

13. The method of claim 1, further comprising ending one or more operations of the wearable device in response to determining that the wearable device has been removed from the user.

14. The method of claim 13, wherein the ending of the one or more operations comprises ending operation of at least one of the one or more biometric sensors of the wearable device.

15. The method of claim 1, further comprising setting a flag associated with output received from at least one of the one or more biometric sensors in response to determining that the wearable device has been removed from the user, the flag indicating that the received output should be verified for accuracy.

16. The method of claim 1, further comprising:
tracking a moving baseline capacitance value based on the output of the capacitive sensor; and
setting an on-wrist baseline value and an off-wrist baseline value relative to the moving baseline capacitance value.

17. The method of claim 16, further comprising:
determining that the moving baseline capacitance value is closer to the off-wrist baseline value than the on-wrist baseline value,
wherein the determining that the wearable device has been removed from the user is further in response to determining that the moving baseline capacitance value is closer to the off-wrist baseline value than the on-wrist baseline value.

18. The method of claim 16, further comprising:
determining that the moving baseline capacitance value is closer to the on-wrist baseline value than the off-wrist baseline value; and
determining that the wearable device is being worn by the user in response to determining that the moving baseline capacitance value is closer to the on-wrist baseline value than the off-wrist baseline value.

19. The method of claim 16, further comprising:
determining that the moving baseline capacitance value has deviated from the on-wrist baseline value by more than a defined percentage; and
wherein the determining that the wearable device has been removed from the user is further in response to determining that the moving baseline capacitance value has deviated from the on-wrist baseline value by more than the defined percentage.

20. The method of claim 16, further comprising:
determining that the moving baseline capacitance value has deviated from the off-wrist baseline value by more than a defined percentage; and
determining that the wearable device is being worn by the user in response to determining that the moving baseline capacitance value has deviated from the off-wrist baseline value by more than a defined percentage.

21. The method of claim 1, wherein the determining that the wearable device has been removed from the user is further in response to output received from at least one of: a skin temperature thermometer; a galvanic skin response sensor; an electromyographic sensor; and an accelerometer.

22. The method of claim 1, wherein the change in the capacitance value comprises a change in a magnitude of the capacitance value within the defined time interval.

23. The method of claim 1, wherein:
the wearable device further comprises (i) a ground plane that shields the capacitive sensor electrode from other circuitry of the wearable device and (ii) an active shield interposed between the capacitive sensor electrode and the ground plane; and the method further comprises driving the active shield and the capacitive sensor electrode at the same potential.

24. A wearable device, comprising:

a capacitive sensor configured to generate an output signal indicative of a distance of the wearable device to a user, the capacitive sensor comprising a capacitive sensor electrode and being configured to generate the output signal based on the distance between the capacitive sensor electrode and the user;

a filter;

at least one processor; and a memory storing computer-executable instructions for controlling the at least one processor to:

attenuate, via the filter, defined frequencies in the output signal of the capacitive sensor;

determine, based at least on the output signal, a capacitive value indicative of the distance of the wearable device to the user;

determine that a change in the capacitance value within a defined time interval is greater than or equal to a threshold change indicative of the wearable device not being proximate to the user's skin;

determine that the wearable device has been removed from the user in response to detecting that the change in the capacitance value within the defined time interval is greater than or equal to the threshold change; and de-authenticate the user from the wearable device in response to determining that the wearable device has been removed from the user.

25. The device of claim 24, further comprising an optical sensor configured to monitor at least one characteristic of the user's heartbeat waveform, wherein the memory further comprises computer-executable instructions for controlling the at least one processor to:

determine that the at least one characteristic of the user's heartbeat waveform is not representative of a cardiac signal, wherein the determining that the wearable device has been removed from the user is further in response to determining that the at least one characteristic of the user's heartbeat waveform is not representative of a cardiac signal.

26. The device of claim 24, wherein the memory further comprises computer-executable instructions for controlling the at least one processor to perform the de-authenticating of the user from the wearable device via de-authorizing mobile payment with the wearable device.

27. The method of claim 1, wherein the filter comprises at least one of a low-pass filter, a band-pass filter, or a high-pass filter.

28. The device of claim 24, wherein the filter comprises at least one of a low-pass filter, a band-pass filter, or a high-pass filter.

* * * * *